United States Patent [19]
Kawaguchi et al.

[11] Patent Number: 5,753,394
[45] Date of Patent: May 19, 1998

[54] TRINITROFLUORENONIMINE DERIVATIVE AND ELECTROPHOTOSENSITIVE MATERIAL USING THE SAME

[75] Inventors: Hirofumi Kawaguchi; Syunichi Matsumoto, both of Osaka, Japan

[73] Assignee: Mita Industrial Co., Ltd., Osaka, Japan

[21] Appl. No.: 561,832

[22] Filed: Nov. 27, 1995

[30] Foreign Application Priority Data

Nov. 30, 1994 [JP] Japan .................. 6-297505
Nov. 30, 1994 [JP] Japan .................. 6-297506
Nov. 30, 1994 [JP] Japan .................. 6-297507

[51] Int. Cl.$^6$ .................................. G03G 5/14
[52] U.S. Cl. ........................... 430/72; 430/73
[58] Field of Search .................. 430/59, 96, 72, 430/73

[56] References Cited

U.S. PATENT DOCUMENTS 4,981,768  1/1991  Monbaliu et al. ................ 430/59

FOREIGN PATENT DOCUMENTS 0615165  3/1994  European Pat. Off. .
1-206349  8/1989  Japan .
5-279582  10/1993  Japan .
6-266128  9/1994  Japan .

Primary Examiner—John Goodrow
Attorney, Agent, or Firm—Beveridge, DeGrandi, Weilacher & Young, L.L.P.

[57] ABSTRACT

The present invention provides a trinitrofluorenonimine derivative represented by the general formula (I):

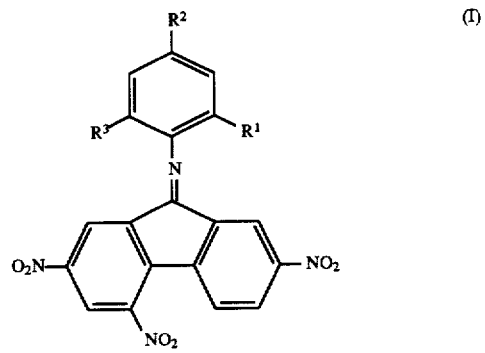

wherein $R^1$, $R^2$ and $R^3$ are the same or different and indicate an alkyl group which may have a substituent.

Such a derivative is superior in electron transferring capability. Accordingly, the electrophotosensitive material having the photosensitive layer containing this derivative is superior in sensitivity.

4 Claims, 8 Drawing Sheets

TRINITROFLUORENONIMINE DERIVATIVE AND ELECTROPHOTOSENSITIVE MATERIAL USING THE SAME

BACKGROUND OF THE INVENTION

The present invention relates to a novel trinitrofluorenonimine derivative, and an electrophotosensitive material which is used for image forming apparatuses such as copying machines, laser beam printers.

As the electrophotosensitive material, the multi-layer type comprising an electric charge generating layer and an electric charge transferring layer, which are mutually laminated, has generally been used, but the single-layer type wherein an electric charge generating material and an electric charge transferring material are dispersed in a single layer, has also been known.

For the electric charge transferring material used in these electrophotosensitive materials, a high carrier mobility is required. Almost all the electric charge transferring materials having a high carrier mobility show hole transferring properties. Therefore, those which can be put into practical use are limited to the negative charging multi-layer type electrophotosensitive material which are provided with an electric charge transferring layer at the outermost layer, from the viewpoint of mechanical strength. Since the negative charging type electrophotosensitive material utilizes negative-polarity corona discharge, large amount of ozone occur, resulting in environmental pollution, the deterioration of the electrophotosensitive material.

In order to remove these defects, it has been studied to use the electron transferring material as an electric charge transferring material. For example, in Japanese Laid-Open Patent Publication No. 1-206349, there is proposed to use the compound having a diphenoquinone structure as an electron transferring material for electrophotosensitive material.

In general, the electron transferring materials such as diphenoquinones are, however, poor in matching with electric charge generating material, resulting in insufficient injection of electrons from the electric charge generating material into the electron transferring material. Therefore, the photosensitivity is insufficient.

The application of the electrophotosensitive material to the single-layer dispersion type can facilitate its production and can prevent layer defects, and also has the advantages for improving the optical characteristics. However, the single-layer type photosensitive layer has the problem that the electron transferring is hindered by the interaction between the diphenoquinone and a hole transferring material.

Regarding the charging polarity of the electrophotosensitive material, its application range broadens if it is possible to use one electrophotosensitive material for both the positive charging and the negative charging types. But such an electrophotosensitive material has never been put into practical use.

In Japanese Laid-Open Patent Publication No. 5-279582, there are disclosed a trinitrofluorenonimine derivative represented by the general formula (3):

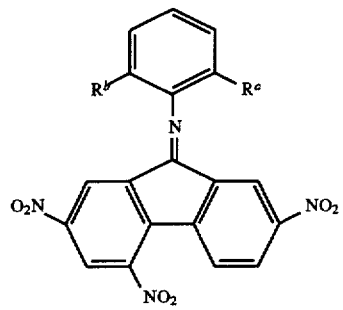

wherein $R^a$ is an alkyl, an alkoxy or an alkyl halid; and $R^b$ is a hydrogen atom, an alkyl, an alkoxy or an alkyl halide, and a multi-layer type electrophotosensitive material containing this derivative as an electron transferring material. The derivative (3) is superior in matching with the electric charge generating material and has the electron transferring capability higher than that of the conventional diphenoquinone compounds. This derivative, however, has the problem that the solubility in solvent and the compatibility with binding resin are insufficient, and therefore, sufficient sensitivity cannot be obtained particularly when it is used for the electrophotosensitive material.

In Japanese Laid-Open Patent Publication No. 6-266128, there is disclosed the fluorenonimine derivative represented by the general formula (4):

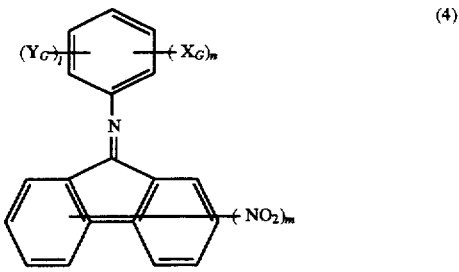

wherein $X_G$ is $—NO_2$, $—OH$, $—CN$, a halogen atom, an aryl or aralkyl group which may have a substituent, $—N(R_G')_2$, $—OR_G'$, $—OCOR_G'$, $—COOR_G'$, $—CONHR_G'$, $—CON(R_G')_2$, $—COR_G'$, $—SOR_G'$ or $—SO_2R_G'$; $Y_G$ is an alkyl group which may have a substituent; $R_G'$ is an alkyl, aryl or aralkyl group which may have a substituent; l, m and n respectively indicate an integer satisfying the following relations: $l \geq 0$, $m \geq 2$, $n \geq 1$, provided that $X_G$ may be the same or different when $n \geq 2$.

The sensitivity of the electrophotosensitive material using a concrete compound of the fluorenonimine derivative represented by the general formula (4) as an electron transferring material is as low as that using the conventional diphenoquinones, as seen from the results of Examples and Comparative Examples described later.

SUMMARY OF THE INVENTION

It is a main object of the present invention to provide a novel compound which is suitable for electron transferring material used in the electrophotosensitive material or the like.

It is another object of the present invention to provide an electrophotosensitive material wherein the injection and the transferring of electrons from an electric charge generating material are smoothly conducted and the sensitivity is improved in comparison with the conventional ones.

In order to improve the solubility in solvent and the compatibility with binding resin which are required for trinitrofluorenonimine derivative, the present inventors have studied intensively about the kind of the substituents being substituted on a base skeleton of the above derivative and its substitution position.

As a result, it has been found that the solubility in solvent and the compatibility with binding resin are improved by substituting a specific substituent on a specific position of a phenyl group substituted on a fluorenilidene ring to improve the asymmetry of molecules so that the solubility and the compatibility are improved, thereby dispersing the trinitrofluorenonimine derivative in the binding resin further uniformly. Therefore, the electron transferring capability of a photosensitive layer is improved, resulting in high sensitivity.

That is, the present invention provides the following trinitrofluorenonimine derivatives represented by the general formula (I):

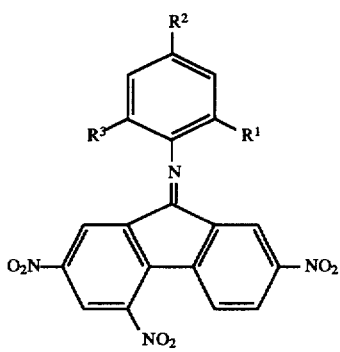

wherein $R^1$, $R^2$ and $R^3$ are the same or different and indicate an alkyl group which may have a substituent; the general formula (II):

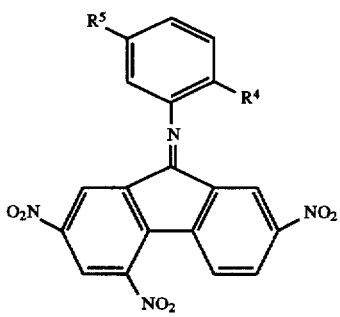

wherein $R^4$ and $R^5$ are the same or different and indicate an alkyl group which may have a substituent; the general formula (III):

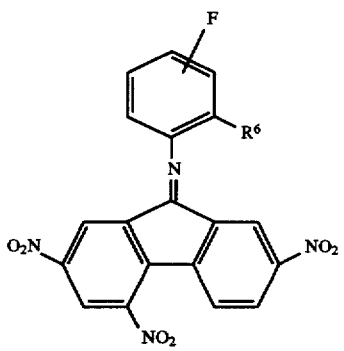

wherein $R^6$ is an alkyl group which may have a substituent; and the general formula (IV):

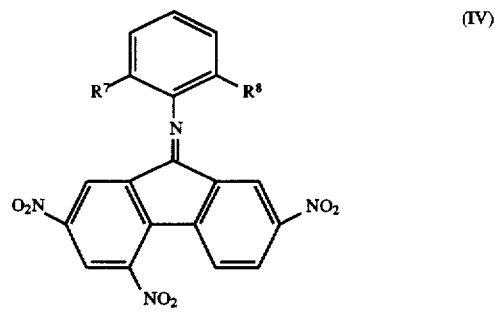

wherein $R^7$ and $R^8$ are the same or different and indicate an alkyl group which may have a substituent.

The trinitrofluorenonimine derivatives represented by the above general formulas (I) to (IV) are superior in solubility in solvent and the compatibility with binding resin.

In addition, the above trinitrofluorenonimine derivatives (I) to (IV) are superior in matching with electric charge generating material (pigment) and, therefore, the injection of electrons are smoothly conducted. Particularly, they are superior in electron transferring properties at low electric field.

Accordingly, the present invention also provide an electrophotosensitive material wherein a photosensitive layer contains a trinitrofluorenonimine derivative selected from the above general formulas (I) to (IV), in a binding resin. This photosensitive material has a sensitivity higher than that of the conventional photosensitive material as previously described.

Furthermore, the trinitrofluorenonimine derivatives represented by the general formulas (I) to (IV) can also be used for applications such as solar batteries and EL devices by making use of their high electron transferring capabilities.

DETAILED DESCRIPTION OF THE INVENTION

Figure 1:
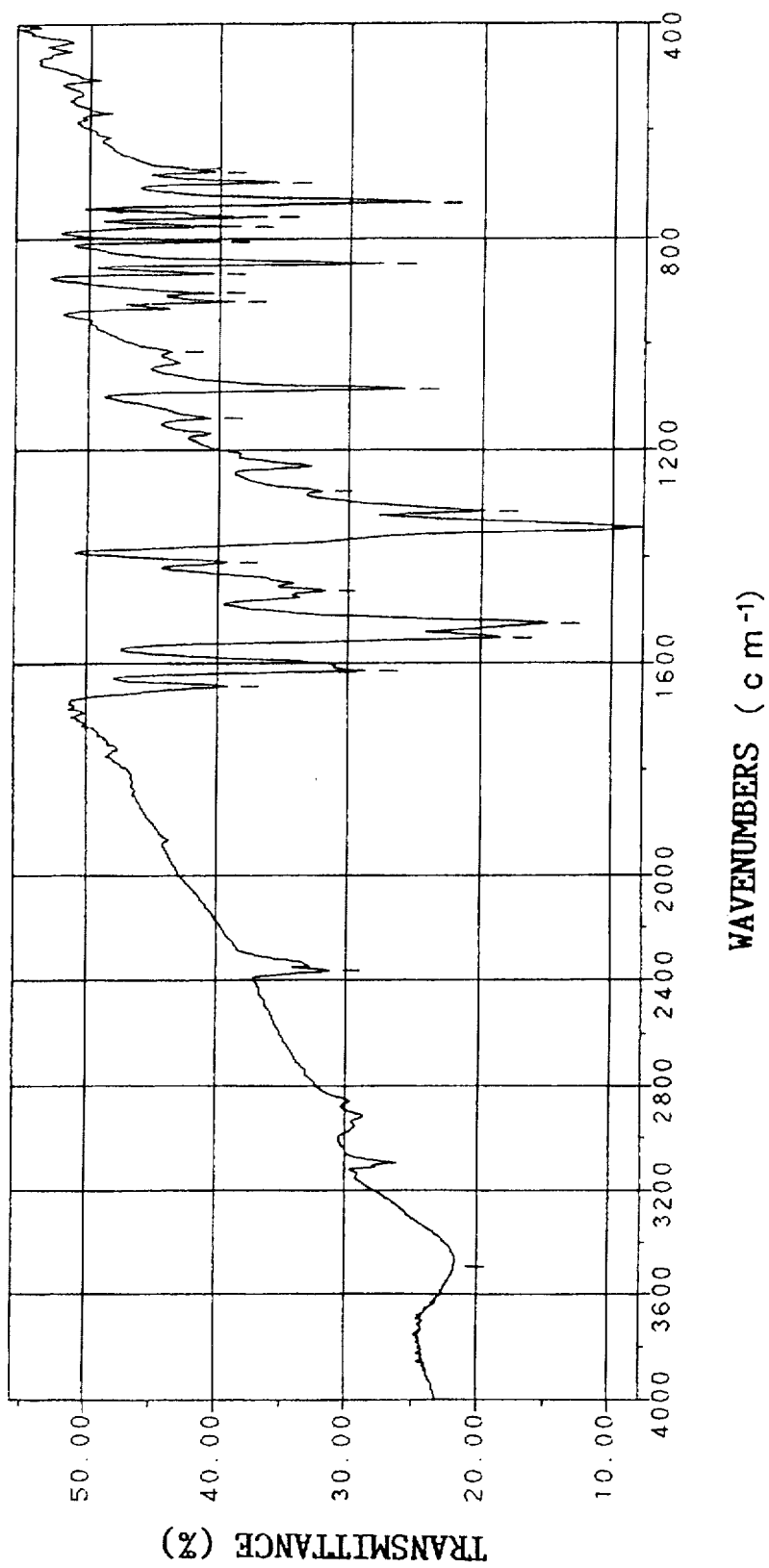
FIG. 1 to FIG. 8 are graphs showing the infrared absorption spectrum of the compound obtained in the Synthetic Examples, respectively.

As the alkyl group, various alkyl groups can be used.

The solubility in solvent and the compatibility with binding resin are apt to be improved as the number of carbon atoms of the alkyl group increases. When the number of carbon atoms of the alkyl group is too large, the alkyl group acts as a plasticizer of the binding resin. Therefore, the surface hardness and the heat resistance of the photosensitive material are likely to be deteriorated. Accordingly, as the above alkyl group, there can be suitably used alkyl groups having 1 to 6 carbon atoms, such as methyl, ethyl, n-propyl, isopropyl, n-butyl, isobutyl, sec-butyl, tert-butyl, pentyl and hexyl.

Examples of the substituents include aryl, aralkyl, alkoxy and halogen atom.

Particularly in the trinitrofluorenonimine derivative of the general formula (1), three alkyl groups are substituted on a phenyl group and, therefore, the solubility and the compatibility can be sufficiently improved even if they are alkyl groups wherein the number of carbon atoms is small, such as methyl and ethyl. Accordingly, the alkyl group having the small number of carbon atoms is preferred, taking the surface hardness and the heat resistance of the photosensitive material into consideration.

The substitution position of the alkyl group $R^6$ in the derivative of the general formula (III) should be limited to the 2-position of the phenyl group. A fluorine atom can be substituted on any position other than the 2-position of the phenyl group. But in view of the reaction yield at the time of synthesizing, the 3- or 5-position is preferred for the 6-position, and the most preferred is the 4-position.

Regarding the alkyl groups $R^7$ and $R^8$ in the derivative of the general formula (IV), different groups are used in combination as described above. When the alkyl groups $R^7$ and $R^8$ are the same, the asymmetry of molecules increases as described above. Therefore, the effect due to the use of the alkyl group as a substituent cannot be adequately exerted, which results in insufficient solubility in solvent and insufficient compatibility with binding resin. Particularly when it is used for the electrophotosensitive material, sufficient sensitivity cannot be obtained.

There are various combinations of the alkyl groups $R^7$ and $R^8$ which differ from each other. Among those, the combinations of the alkyl groups having the small number of carbon atoms, such as the combination of methyl and ethyl, and that of methyl and propyl, are preferred because the derivative is readily produced and the structure is simple.

In addition, the combination of the alkyl groups having the small number of carbon atoms have the advantage that the effect of improving the solubility and the compatibility of the derivative can be efficiently developed. That is, in the combination of the alkyl groups having the large number of carbon atoms, the influence on the asymmetry of molecules is weak even when the difference in number of the carbon atoms is 1 or 2. Whereas in the alkyl group having the large number of carbon atoms, i.e., in a range of 1 to 3, the influence on the asymmetry of molecules is strong even when the difference in number of the carbon atoms is 1 or 2, thereby noticeably improving the solubility and the compatibility of the derivative.

Furthermore, in the combination of the alkyl groups having the small number of carbon atoms, there is no possibility that the surface hardness and the heat resistance of the photosensitive material are deteriorated.

The derivative represented by the general formula (1) is synthesized by condensing 2,4,7-trinitrofluorenone with an aniline substituted with three alkyl groups in a suitable solvent, as shown in the following reaction scheme. Examples of the solvents include acetic acid, propionic acid, butanoic acid, chloroform, tetrahydrofuran, dimethylformamide and dimethyl sulfoxide. If necessary, the reaction may be conducted in the presence of a suitable catalyst such as zinc oxide. The reaction may be normally conducted at a temperature of 30° to 170° C. for about 20 minutes to 4 hours.

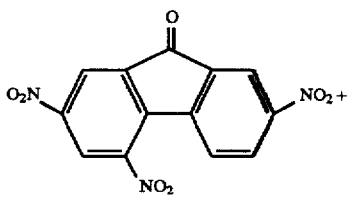

(I)

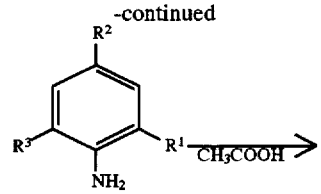

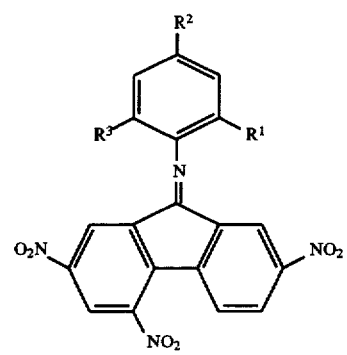

wherein $R^1$, $R^2$ and $R^3$ are as defined above.

Examples of the trinitrofluorenonimine derivatives represented by the general formula (1) include the compound represented by the following formula (I-1):

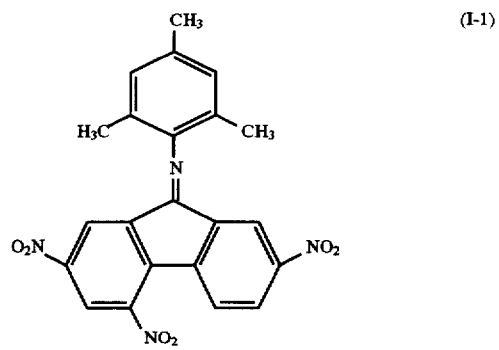

(I-1)

In order to synthesize the derivative represented by the general formula (II), the reaction may be conducted using an aniline substituted with two alkyl groups represented by the following formula (A) in place of the aniline substituted with three alkyl groups in the above reaction scheme, according to the same manner as that of the above reaction scheme.

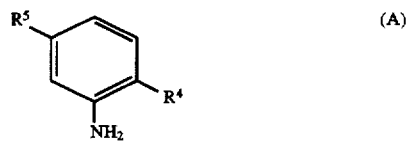

(A)

wherein $R^4$ and $R^5$ are as defined above.

Examples of the trinitrofluorenonimine derivatives represented by the general formula (II) include the compounds represented by the following formulas (II-1) and (II-2).

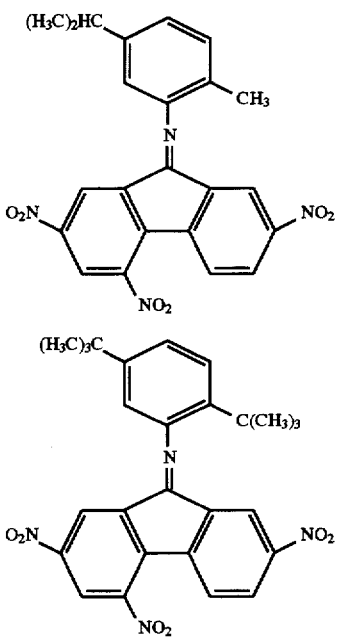

(II-1)

(II-2)

In order to synthesize the derivatives represented by the general formulas (III) and (IV), the reaction may be conducted using aniline derivatives represented by the following formula (B) and (C) in place of the aniline substituted with three alkyl groups in the above reaction scheme, respectively, according to the same manner as that of the above reaction scheme.

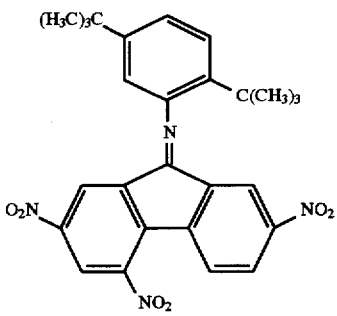

(B)

(C)

Examples of the trinitrofluorenonimine derivatives represented by the general formula (III) include the compounds represented by the following formulas (III-1) to (III-3).

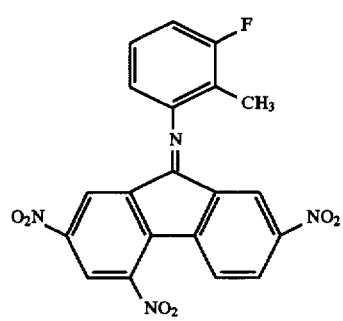

(III-1)

-continued (III-2)

(III-3)

Examples of the trinitrofluorenonimine derivative represented by the general formula (IV) include the compounds represented by the following formulas (IV-1) and (IV-2).

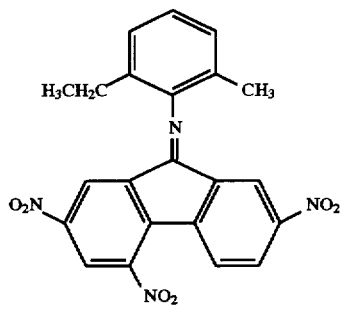

(IV-1)

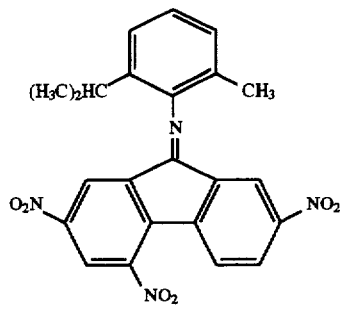

(IV-2)

Hereinafter the electrophotosensitive material of the present invention will be described.

The electrophotosensitive material of the present invention has a photosensitive layer provided on a conductive substrate, the photosensitive layer containing, as an electron transferring material, one or more sorts of the trinitrofluorenonimine derivatives represented by the general formula (I) to (IV) in a binding resin.

The photosensitive layer may be classified into two types: the single-layer type containing an electric charge generating material and a hole transferring material; the multi-layer type comprising an electric charge transferring layer and an electric charge generating layer.

The photosensitive material of the present invention is applicable to both the positive and the negative charging types, but the positive charging type is preferred.

In the positive charging type photosensitive material, electrons emitted from the electric charge generating material in the exposure process are smoothly injected into the above electron transferring material, and then transferred to the surface of the photosensitive layer by the transfer of the electrons between the electron transferring materials, thus canceling the positive electric charge (+) which has previously been charged on the surface of the photosensitive layer. On the other hand, holes (+) are injected into the hole transferring material and transferred to the surface of the conductive substrate without being trapped on the way, and then the holes are canceled by the negative charge (−) which has previously been charged on the surface of the conductive substrate. Thus in this manner, it is regarded that the sensitivity of the positive charging type photosensitive material can be improved.

As the hole transferring material, there can be used the known hole transferring materials, for example, diamine compounds; oxadiazole compounds such as 2,5-di(4-methylaminophenyl)-1,3,4-oxadiazole; organic polysilane compounds; styryl compounds such as 9-(4-diethylaminostyryl)anthracene; carbazole compounds such as polyvinyl carbazole; pyrazoline compounds such as 1-phenyl-3-(p-dimethylaminophenyl)pyrazoline; hydrazone compounds; triphenylamine compounds; indol compounds; oxazole compounds; isoxazole compounds, thiazole compounds; thiadiazole compounds, imidazole compounds; pyrazole compounds; nitrogen-containing cyclic compounds such as triazole compound; and polycyclic compounds.

These hole transferring materials are used alone or in combination. When using the hole transferring material having layer-forming properties, such as polyvinyl carbazole, a binding resin is not necessarily required.

Among the above hole transferring materials, those having an ionization potential of 5.0 to 5.6 eV are preferred. The most preferred are those having the mobility of not less than $1 \times 10^{-6}$ cm$^2$/V.s at the electric field strength of $3 \times 10^5$ V/cm.

The ionization potential was measured using a photoelectric analytical apparatus (Model AC-1, manufactured by Riken Instrument Co., Ltd.) under atmosphere.

Examples of the hole transferring materials suitably used in the present invention include N,N,N',N'-tetrakis(p-methylphenyl)-3,3'-dimethylbenzidine, 1,1-bis(4-diethylaminophenyl)-4,4'-diphenyl-1,3-butadiene, N-ethyl-3-carbazolylaldehyde diphenylhydrazone, p-N,N-diethylbenzaldehyde diphenylhydrazone, 4-[N,N-bis(p-toluyl)amino]-β-phenylstilbene, among others.

In the present invention, the residual potential can be further lowered to improve the sensitivity by using the hole transferring material having the ionization potential within the above range. The reason for this needs further clarification, but it can be considered as follows.

Specifically, the ease in the injecting electric charge from the electric charge generating material into the hole transferring material has a close relation with the ionization potential of the hole transferring material. When the value of the ionization potential exceeds the above range, the degree of the injection of electric charge from the electric charge generating material into the hole transferring material lowers, or the degree of the hole transfer between the hole transferring materials lowers, resulting in deterioration of the sensitivity.

On the other hand, in the system wherein the hole transferring material and the electron transferring material coexist, special care should be given to the interaction between the two, more particularly the formation of a charge transfer complex. When such a complex is formed between them, the recombination between holes and electrons occurs, lowering the mobility of the electric charge on the whole. When the value of the ionization potential of the hole transferring material is below the above range, the tendency to form a complex between the hole transferring material and the electron transferring material is enhanced to cause the recombination between the electrons and the holes. Then an apparent yield of quantums lowers, leading to the deterioration of the sensitivity. Therefore it is preferred that the ionization potential of the hole transferring material is within the above range.

Examples of the electric charge generating material include selenium, selenium-tellurium, amorphous silicon, pyrilium salt, azo pigments, bisazo pigments, anthanthrone pigments, phthalocyanine pigments, naphthalocyanine pigments, indigo pigments, triphenylmethane pigments, threne pigments, toluidine pigments, pyrazoline pigments, quinacridone pigments and dithioketopyrrolopyrrole pigments. One or more sorts of these electric charge generating materials may be used in combination in order to obtain an absorption wavelength within a desired region.

As the electric charge generating materials suitable for the photosensitive material having the sensitivity at the wavelength region of not less than 700 nm, which is particularly used for digital-optical image forming apparatuses, there are, for example, phthalocyanine pigments such as X-type metal-free phthalocyanine and oxotitanyl phthalocyanine. Since these phthalocyanine pigments are superior in matching with the trinitrofluorenonimine derivative of the present invention served as an electron transferring material, the electrophotosensitive material using both in combination shows a high sensitivity within the above wavelength region. Therefore it can be suitably used for digital-optical image forming apparatuses such as laser beam printers and facsimiles.

In connection with the use of the hole transferring material having the ionization potential of from 5.0 to 5.6 eV, the above phthalocyanine pigments preferably have the ionization potential being balanced with that of the hole transferring material. That is, 5.0 to 5.6 eV is preferred, particularly 5.32 to 5.38 eV, in view of the lowering of the residual potential and the improvement of the sensitivity.

On the other hand, as the electric charge generating material suitable for the photosensitive material having a high sensitivity in the visible region, which is used for analog-optical image forming apparatuses, there are, for example, a perylene pigment represented by the general formula (5):

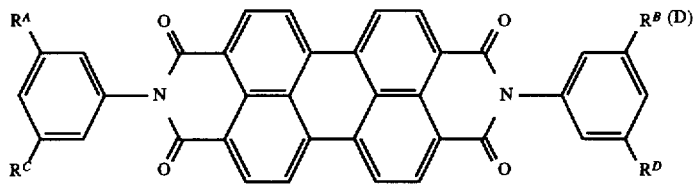

wherein $R^A$, $R^B$, $R^C$ and $R^D$ are the same or different and indicate a hydrogen atom, an alkyl, an alkoxy or an aryl. This perylene pigment has a high sensitivity in the visible region and is superior in matching with the trinitrofluorenonimine derivative of the present invention served as an electron transferring material. Therefore, the electrophotosensitive material using both in combination has a high sensitivity in the visible region, and therefore, it can be suitably used for analog-optical image forming apparatuses such as electrostatic copying machines.

In connection with the use of the hole transferring material having the ionization potential of from 5.0 to 5.6 eV, the above perylene pigment preferably has the ionization potential being balanced with that of the hole transferring material. That is, 5.0 to 5.6 eV is preferred, particularly 4.8 to 5.8 eV, in view of the lowering of the residual potential and the improvement of the sensitivity.

As the binding resin for dispersing the above respective components, various known resins for the photosensitive layer can be used. There are, for example, thermoplastic resins such as styrene polymer, styrene-butadiene copolymer, styrene-acrylonitrile copolymer, styrene-maleic acid copolymer, acrylic copolymer, styrene-acrylic acid copolymer, polyethylene, ethylene-vinyl acetate copolymer, chlorinated polyethylene, polyvinyl chloride, polypropylene, ionomer, vinyl chloride-vinyl acetate copolymer, polyester, alkyd resin, polyamide, polyurethane, polycarbonate, polyarylate, polysulfon, diaryl phthalate resin, ketone resin, polyvinyl butyral resin, polyether resin, polyester resin; crosslinking thermosetting resins such as silicone resin, epoxy resin, phenol resin, urea resin and melamine resin; photosetting resins such as epoxy acrylate and urethane acrylate. These binding resins can be used alone or in combination. The suitable resins are styrene polymer, acrylic polymer, styrene-acrylic copolymer, polyester, alkyd resin, polycarbonate and polyarylate.

To the photosensitive layer, various known additives can be blended without adverse effect on the electrophotographic characteristics. There are, for example, deterioration inhibitors (e.g., antioxidants, radical scavengers, singlet quenchers, ultraviolet absorbers), softeners, plasticizers, surface modifiers, bulking agents, thickening agents, dispersion stabilizers, wax, acceptors and donors. The amount of these additives may be the same as that of the conventional ones. For example, a steric hindered phenolic antioxidant is preferably blended in an amount of about 0.1 to 50 parts by weight, based on 100 parts by weight of the binding resin.

In order to improve the sensitivity of the photosensitive layer, known sensitizers such as terphenyl, halonaphthoquinones and acenaphthylene may be used in combination with the electric charge generating material.

In addition, other known electron transferring materials can be used in combination with the trinitrofluorenonimine derivatives represented by the above general formulas (I), (II), (III) and (IV). There are, for example, benzoquinone compounds, diphenoquinone compounds, malononitrile compounds, thiopyran compounds, tetracyanoethylene, 2,4,8-trinitrothioxanthone, fluorenone compounds (e.g., 3,4,5,7-tetranitro-9-fluorenone), dinitrobenzene, dinitroanthracene, dinitroacridine, nitroanthraquinone, dinitroanthraquinone, succinic anhydride, maleic anhydride and dibromomaleic anhydride.

As the conductive substrate used for the photosensitive material of the present invention, various materials having conductivity can be used. There are, for example, metals such as aluminum, copper, tin, platinum, silver, vanadium, molybdenum, chromium, cadmium, titanium, nickel, palladium, indium, stainless steel and brass; plastic materials vapor-deposited or laminated with the above metal; and glass materials coated with aluminum iodide, tin oxide, indium oxide or the like.

The conductive substrate may be made in the form of a sheet or a drum. The substrate itself may have conductivity, or only the surface of the substrate may have conductivity. The conductive substrate preferably has sufficient mechanical strength when it is used.

The photosensitive layer in the present invention is produced by applying and drying a coating solution, which is obtained by dissolving or dispersing a resin composition containing the above respective components in a suitable solvent, on a conductive substrate.

The effect due to the use of the trinitrofluorenonimine derivative of the present invention develops noticeably in the single-layer type photosensitive material. The single-layer type photosensitive material is applicable to both the positive and the negative charging types, but the former is preferred.

In the single-layer type photosensitive material, it is preferred that the electric charge generating material is blended in an amount of 0.1 to 50 parts by weight, particularly 0.5 to 30 parts by weight, based on 100 parts by weight of the binding resin.

It is preferred that the hole transferring material is blended in an amount of 5 to 500 parts by weight, particularly 25 to 200 parts by weight, based on 100 parts by weight of the binding resin.

It is preferred that the electron transferring material is blended in an amount of 5 to 100 parts by weight, particularly 10 to 80 parts by weight, based on 100 parts by weight of the binding resin.

When using only one or more sorts of the trinitrofluorenonimine derivatives of the present invention as an electron transferring material, the amount of the electron transferring material should fall under the above range. When using in combination with another electron transferring material, the total amount should fall under the above range.

The single-layer type electrophotosensitive material preferably has a thickness of about 5 to 100 μm, particularly about 10 to 50 μm.

In order to obtain the multi-layer type electrophotosensitive material, the electric charge generating layer may be formed by depositing an electric charge generating material alone on a conductive substrate, or an electric charge generating layer containing the electric charge generating material, the binding resin and, if necessary, the hole transferring material, may be formed by application or the like.

and then an electric charge transferring layer containing the compound of the present invention being electron transferring material and the binding resin may be formed on the electric charge generating layer. To the contrary, the electric charge transferring layer may be formed on the conductive substrate, and then the electric charge generating material is formed thereon.

In the multi-layer photosensitive material, the electric charge generating material and the binding resin which constitute the electric charge generating layer, may be used in various proportions, but an amount of from 5 to 1000 parts by weight is preferred, particularly 30 to 500 parts by weight, based on 100 parts by weight of the binding resin.

The electron transferring material and the binding resin which constitute the electric charge transferring layer, can be used in various proportions without inhibiting the transfer of electrons and without causing the crystallization. But in order to facilitate the transfer of the electrons generated by light irradiation in the electric charge generating layer, it is preferred to use an amount of from 10 to 500 parts by weight, particularly 25 to 200 parts by weight, based on 100 parts by weight of the binding resin.

Like in the above single-layer type photosensitive material, when using only one or more sorts of the trinitrofluorenonimine derivatives of the present invention as an electron transferring material, the amount of the electron transferring material should fall under the above range. When using in combination with another electron transferring material, the total amount should fall under the above range.

In the multi-layer type photosensitive layer, the electric charge generating layer preferably has a thickness of about 0.01 to 5 μm, particularly about 0.1 to 3 μm, and the electric charge transferring layer preferably has a thickness of about 2 to 100 μm, particularly about 5 to 50 μm.

A barrier layer may be formed, without inhibiting the characteristics of the electrophotosensitive material, between the conductive substrate and the photosensitive layer in the single-layer type photosensitive material, or between the conductive substrate and the electric charge generating layer or between the conductive substrate layer and the electric charge transferring layer in the multi-layer type photosensitive material. In addition, a protective layer may be formed on the surface of the photosensitive layer.

In order to form the above photosensitive layer by application, the electric charge generating material, the electric charge transferring material and the binding resin as previously described may be dispersed and mixed with a suitable solvent by the known methods, for example, a roll mill, a ball mill, an atriter, a paint shaker or a supersonic dispenser, to prepare a dispersion liquid, which is then applied and dried by the known means.

As the solvent for preparing the dispersion liquid, there can be used various organic solvents. There are, for example, alcohols such as methanol, ethanol, isopropanol and butanol; aliphatic hydrocarbons such as n-hexane and octane, cyclohexane; aromatic hydrocarbons such as benzene, toluene and xylene; hydrocarbon halides such as dichloromethane, dichloroethane, carbon tetrachloride and chlorobenzene; ethers such as dimethyl ether, diethyl ether, tetrahydrofuran, ethylene glycol dimethyl ether and diethylene glycol dimethyl ether; ketones such as acetone, methyl ethyl ketone and cyclohexanone; esters such as ethyl acetate and methyl acetate; dimethylformaldehyde, dimethylformamide and dimethyl sulfoxide. These solvents may be used alone or in combination.

In order to improve the dispersibility of the electric charge transferring material and the electric charge generating material, as well as the smoothness of the surface of the photosensitive layer, there may be used surfactants, leveling agents and the like.

EXAMPLES

The invention will be better understood by the following Examples and Comparative Examples which show by way of example.

Synthesis Example 1

Production of N-mesityl-2,4,7-trinitrofluorenonimine 2,4,7-Trinitrofluorenonimine (3.15 g, 10 mmols) and mesidine (2.03 g, 15 mmols) were dissolved in 50 ml of acetic acid, and the mixture was reacted at 110° C. for 2 hours.

After the completion of the reaction, the reaction solution was added to 300 ml of water to deposit a crystal. The crystal was filtered, washed with water, and then purified by subjecting to silica gel column chromatography (chloroform-hexane mixed system) to obtain 2.7 g of the titled compound represented by the above formula (I-1) (yield: 63%).

The melting point of this compound was 192° C.

The electron transferring capability of the above compound was evaluated by TOF method. As a result, it has been found that the compound has a high electron transferring capability because it showed the mobility of $5.54 \times 10^{-7}$ cm$^2$/V.s at the electric field strength of $3 \times 10^5$ V/cm.

The infrared absorption spectrum of the above compound is shown in FIG. 1.

Synthesis Example 2

Production of N-(2-methyl-5-isopropylphenyl)-2,4,7-trinitrofluorenonimine

According to the same manner as that described in Synthesis Example 1 except for using 2-methyl-5-isopropylaniline (2.24 g, 15 mmols) in place of the mesidine, 2.5 g of the titled compound represented by the above formula (II-1) was obtained (yield: 56%).

The melting point of this compound was 156° C.

The electron transferring capability of the above compound was evaluated by TOF method. As a result, it has been found that the compound has a high electron transferring capability because it showed the mobility of $6.18 \times 10^{-7}$ cm$^2$/V.s at the electric field strength of $3 \times 10^5$ V/cm.

Figure 2:
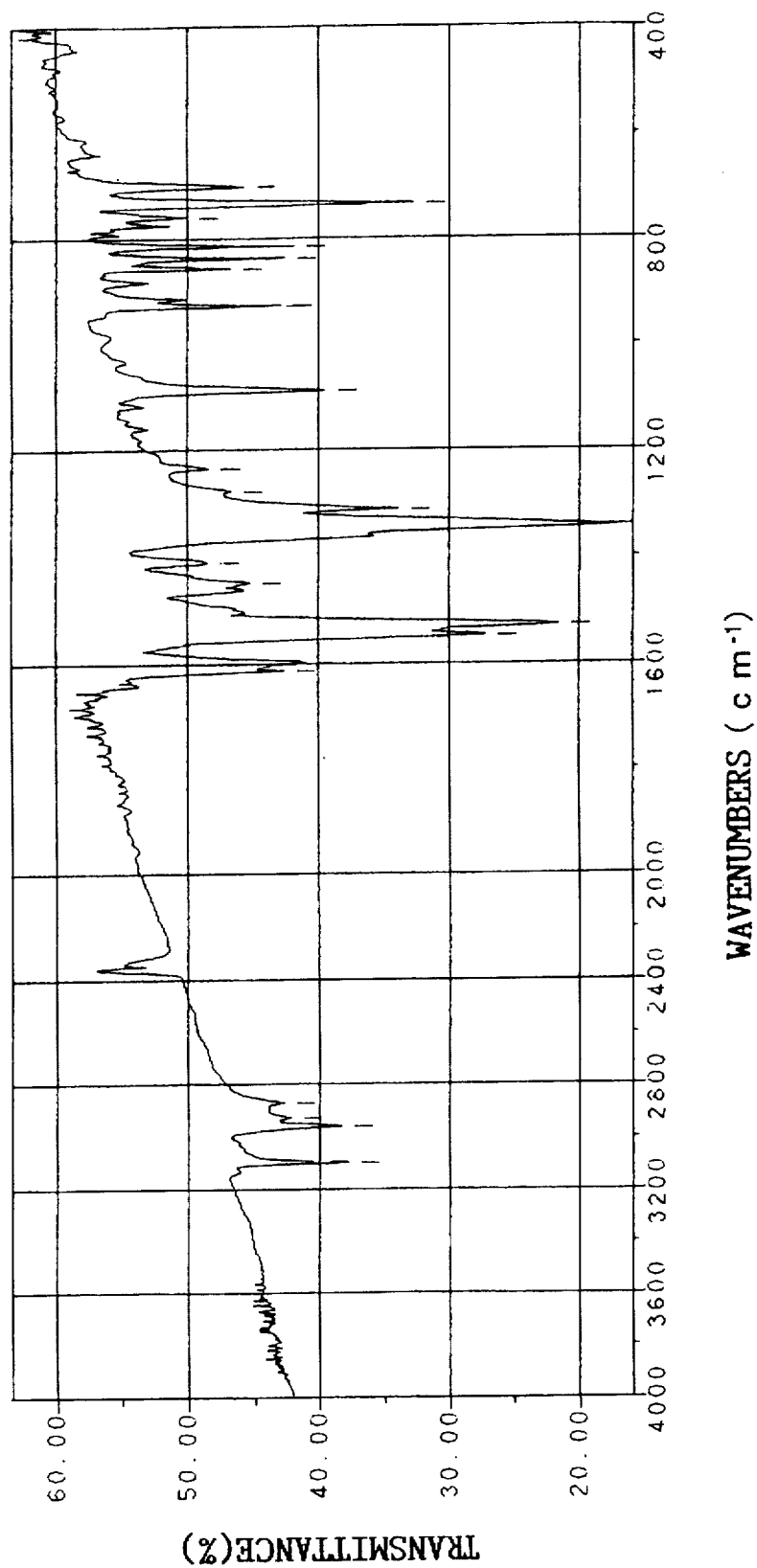

The infrared absorption spectrum of the above compound is shown in FIG. 2.

Synthesis Example 3

Production of N-(2,5-di-tert-butylphenyl)-2,4,7-trinitrofluorenonimine

According to the same manner as that described in Synthesis Example 1 except for using 2,5-di-tert-butylaniline (3.08 g, 15 mmols) in place of the mesidine, 2.7 g of the titled compound represented by the above formula (II-2) was obtained (yield: 53%).

The melting point of this compound was 214° C.

The electron transferring capability of the above compound was evaluated by TOF method. As a result, it has been found that the compound has a high electron transferring capability because it showed the mobility of $7.11 \times 10^{-7}$ cm$^2$/V.s at the electric field strength of $3 \times 10^5$ V/cm.

Figure 3:
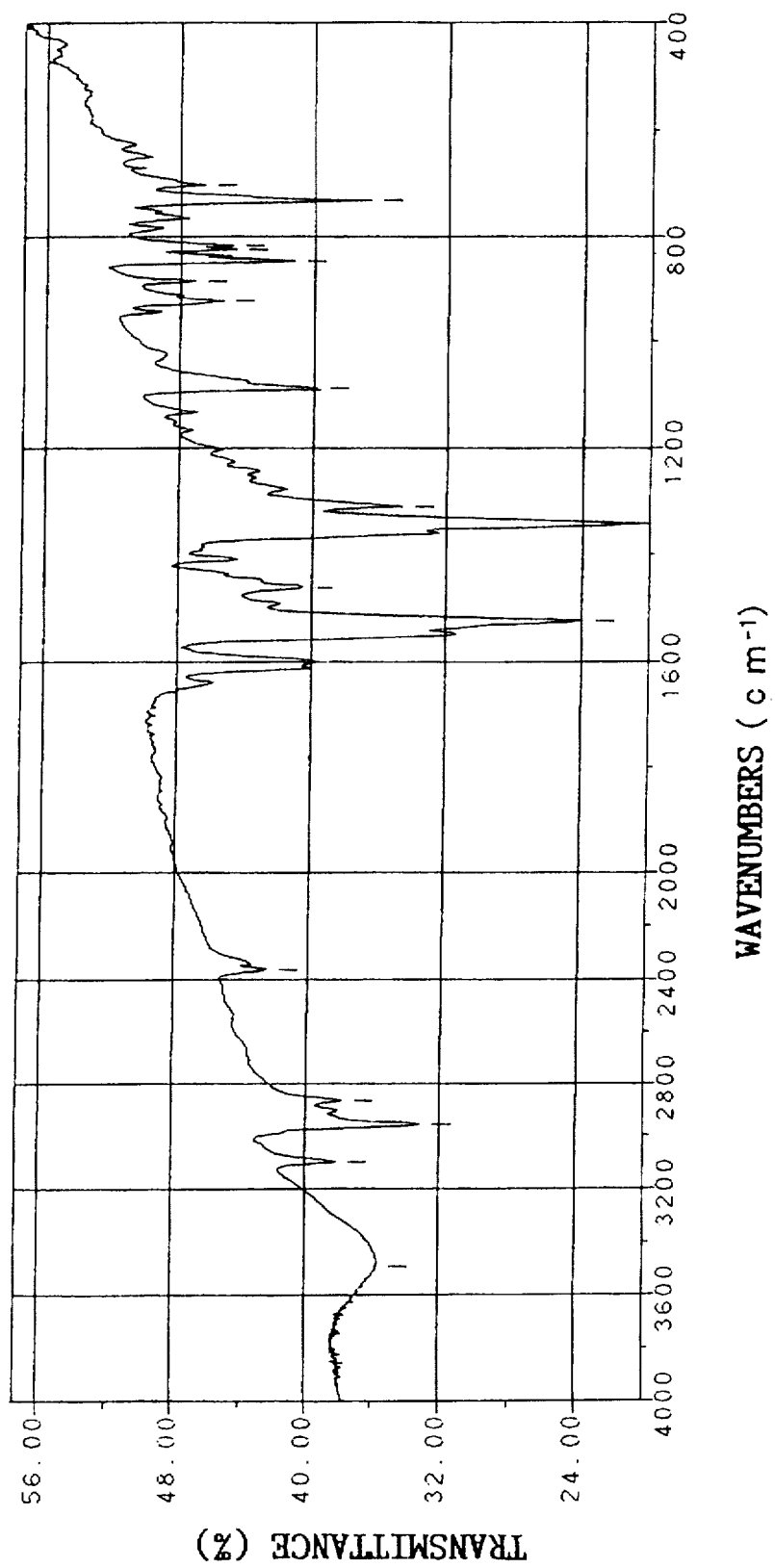

The infrared absorption spectrum of the above compound is shown in FIG. 3.

Solubility and Compatibility Tests

Regarding the compounds obtained in Synthesis Examples 1 to 3 and Comparative compounds which belong to the conventional fluorenonimine derivatives, the solubility in tetrahydrofuran being solvent and the compatibility with polycarbonate being binding resin were evaluated by the following test method.

<Test method>

100 Parts by weight of polycarbonate and 80 parts by weight of a test compound (i.e., the compounds in Synthesis Examples 1 to 3 or the comparative compounds described later) were mixed and dispersed, together with 800 parts by weight of tetrahydrofuran using a ball mill for 2 hours to prepare a test solution. Then, this solution was observed visually to evaluate the solubility in tetrahydrofuran according to the following three-level criteria.

○: An uniform solution was obtained (good solubility).

△: An insoluble matter was observed in parts of the solution (slightly inferior solubility).

X: An insoluble matter was observed over the whole solution (inferior solubility).

Then, the above test solution was applied on the surface of an aluminum foil using a wire bar, followed by hot-air drying at 100° C. for 60 minutes to form a layer having a thickness of 15 to 20 μm. This layer was observed visually to evaluate the compatibility with the polycarbonate of the test compound according to the following three-level criteria.

○: An uniform solution was obtained (good compatibility).

△: Crystallization was observed in parts of the solution (slightly inferior compatibility)

X: Crystallization was observed over the whole solution (inferior compatibility).

The results are shown in Table 1.

The following compounds were used as a comparative compound.

(i) Compounds, which belong to the conventional trinitrofluorenonimine derivative represented by the above general formula (3), being represented by the following formulas (3-1) to (3-3):

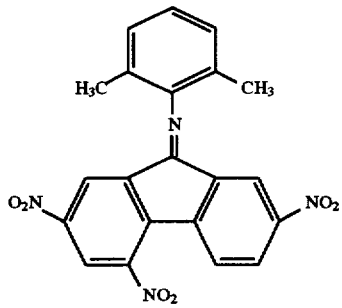
(3-1)

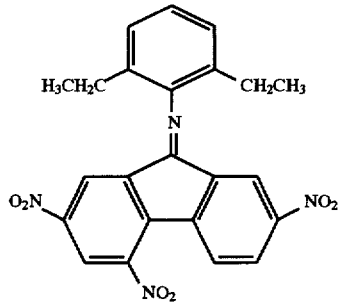
(3-2)

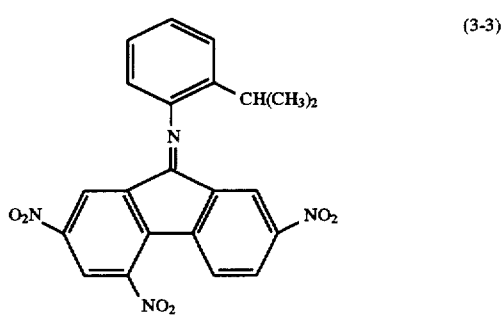
(3-3)

(ii) Compounds, which belong to the fluorenonimine derivative represented by the above general formula (4) disclosed in Japanese Laid-Open Patent Publication No. 6-266128, being represented by the following formulas (4-1) to (4-3):

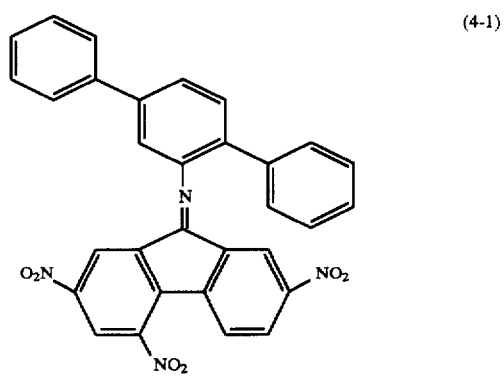
(4-1)

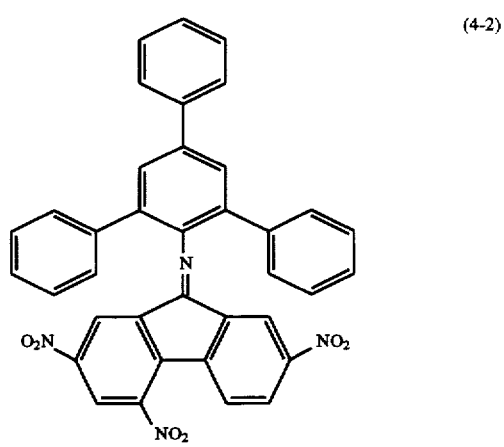
(4-2)

(4-3)
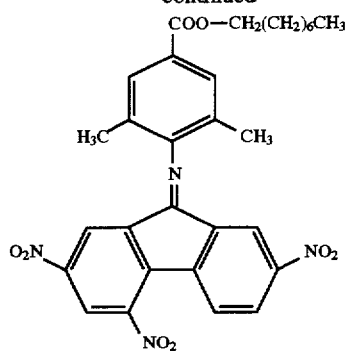
(iii) The other compounds than the derivative of the above general formula (4) in the Publication No. 6-266128, being represented by the following formulas:
(7-1)
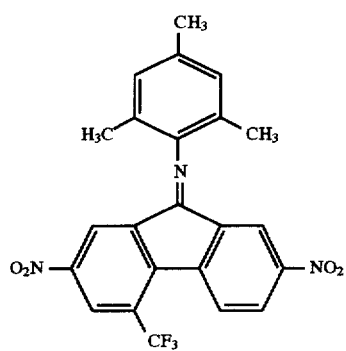
(7-2)
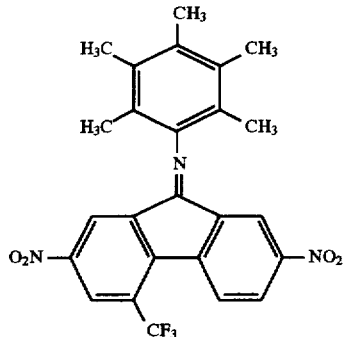
(7-3)
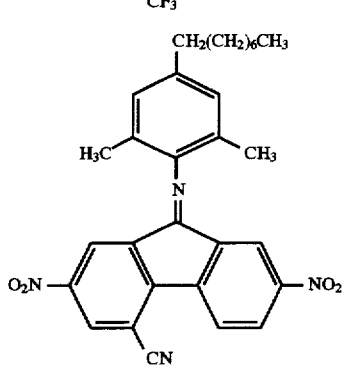
(8-1)
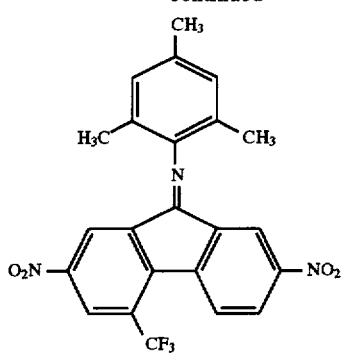
(8-2)
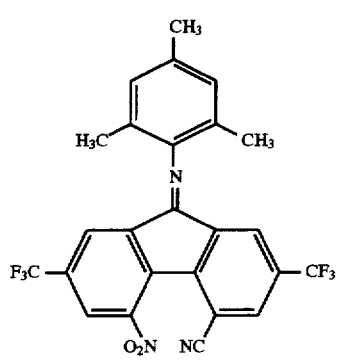
(9-1)
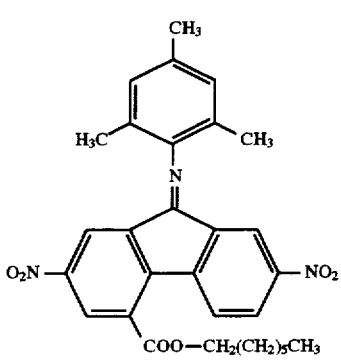
(9-2)
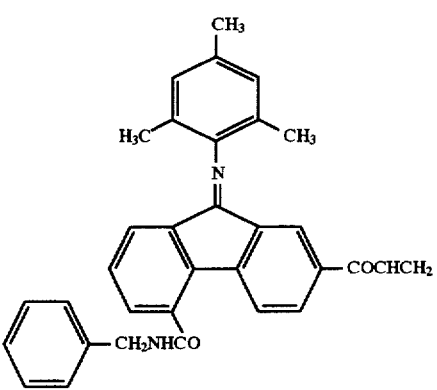

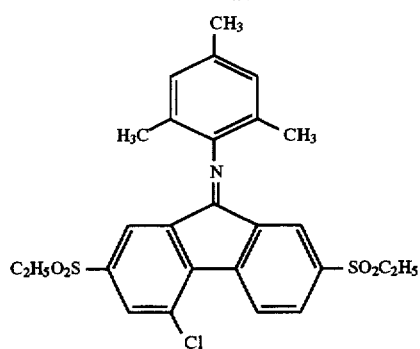
(10-1)
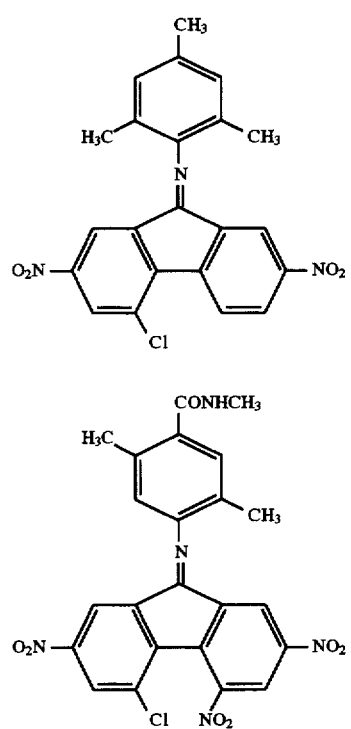
(11-1)
(11-2)
(11-3)
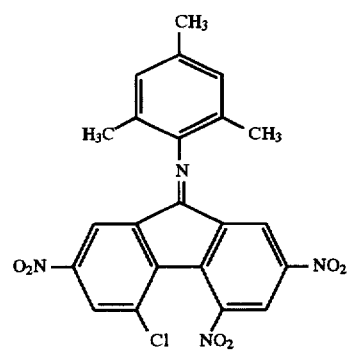
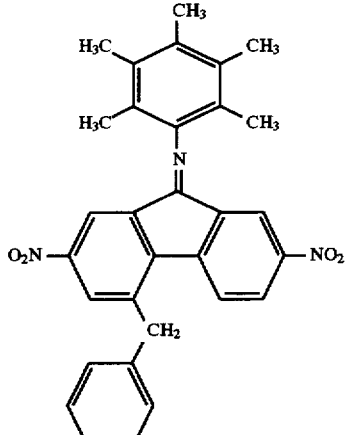
(12-1)
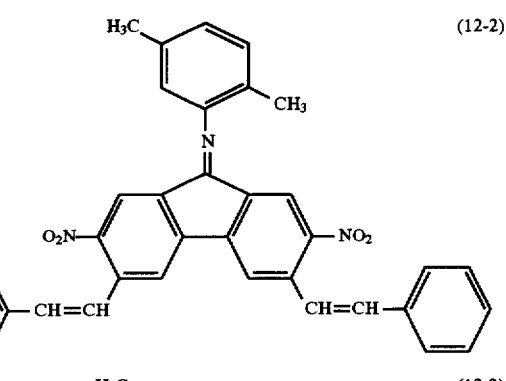
(12-2)
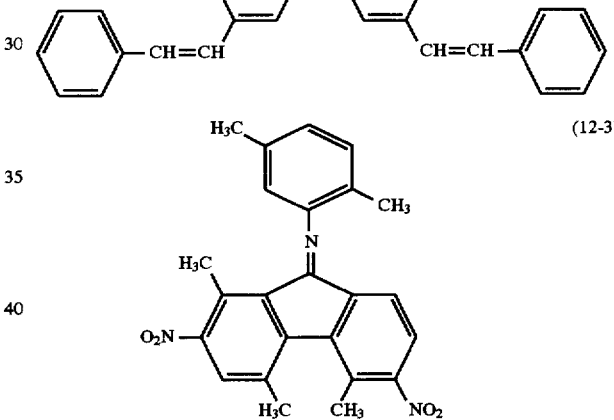
(12-3)
TABLE 1
| Test Compound | Solubility | Compatibility |
|---|---|---|
| I-1 | ○ | ○ |
| II-1 | ○ | ○ |
| II-2 | ○ | ○ |
| 3-1 | ○ | Δ |
| 3-2 | ○ | Δ |
| 3-3 | ○ | Δ |
| 4-1 | × | × |
| 4-2 | × | × |
| 4-3 | ○ | Δ |
| 7-1 | ○ | × |
| 7-2 | ○ | × |
| 7-3 | ○ | Δ |
| 8-1 | Δ | × |
| 8-2 | × | × |
| 9-1 | ○ | Δ |
| 9-2 | Δ | × |
| 10-1 | × | × |
| 11-1 | × | × |
| 11-2 | × | × |
| 11-3 | Δ | × |
| 12-1 | × | × |

TABLE 1-continued

| Test Compound | Solubility | Compatibility |
|---|---|---|
| 12-2 | × | × |
| 12-3 | ○ | Δ |

<Single-layer type photosensitive material for digital light source>

Example 1 to 6

5 Parts by weight of X-type metal-free phthalocyanine (Xφ, Ip=5.38 eV) or oxotitanyl phthalocyanine (Tiφ, Ip=5.32 eV) as an electric charge generating material, 30 parts by weight of the trinitrofluorenonimine derivative represented by the above formula (I-1), (II-1) or (II-2) in Synthesis Examples 1 to 3 as an electron transferring material, 50 parts by weight of N,N,N',N'-tetrakis(p-methylphenyl)-3,3'-dimethylbenzidine (Ip=5.56 eV) represented by the formula (6):

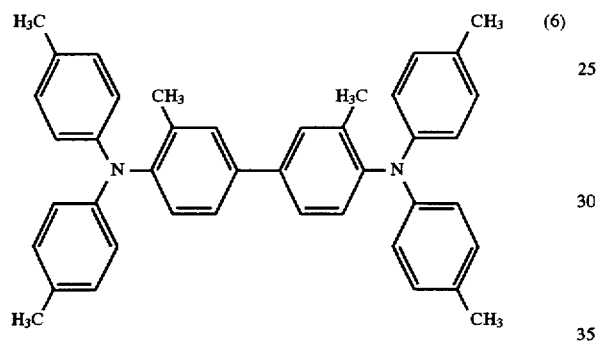

as a hole transferring material, 100 parts by weight of polycarbonate as a binding resin and 800 parts by weight of tetrahydrofuran were mixed and dispersed using a ball mill for 50 hours to prepare a coating solution for single-layer type photosensitive layer. Then, this solution was applied on the surface of an aluminum tube being conductive substrate by dip coating, followed by hot-air drying at 100° C. for 60 minutes to obtain each electrophotosensitive material having a single-layer type photosensitive layer for digital light source, whose mean thickness is 17 μm.

Comparative Examples 1 to 3

According to the same manner as that described in Examples 1 to 6 except for using 30 parts by weight of any one of the compounds represented by the above formulas (3-1) to (3-3) as an electron transferring material, each electrophotosensitive material having a single-layer type photosensitive layer for digital light source was produced.

Comparative Examples 4 to 33

According to the same manner as that described in Examples 1 to 6 except for using 30 parts by weight of any one of the compounds represented by the above formulas (4-1) to (4-3) and compounds represented by the following formulas (4-4) to (4-30), which belong to the fluorenonimine derivative represented by the above general formula (4) in the Publication No. 6-266128, as an electron transferring material, each electrophotosensitive material having a single-layer type photosensitive layer for digital light source was produced.

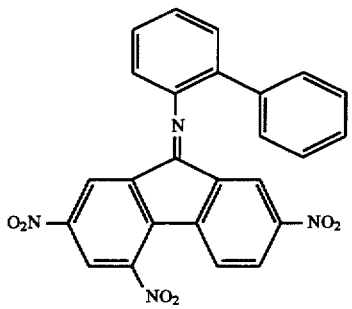
(4-4)

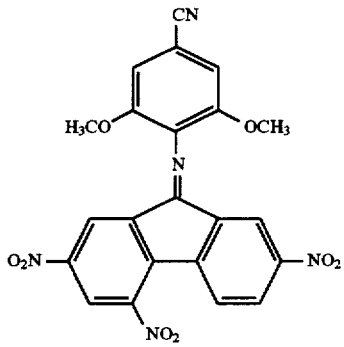
(4-5)

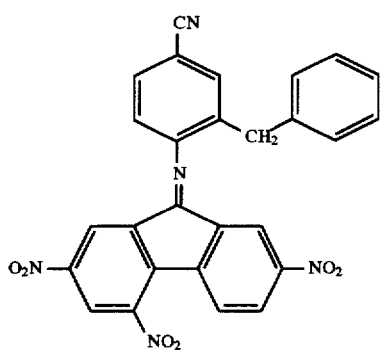
(4-6)

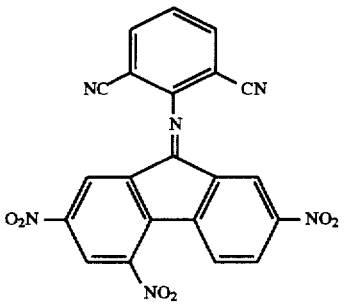
(4-7)

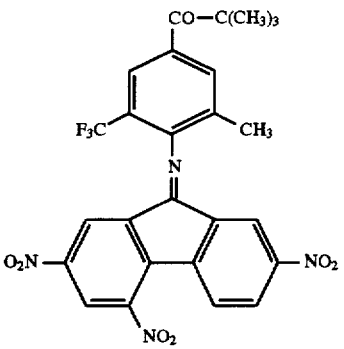
(4-8)

-continued
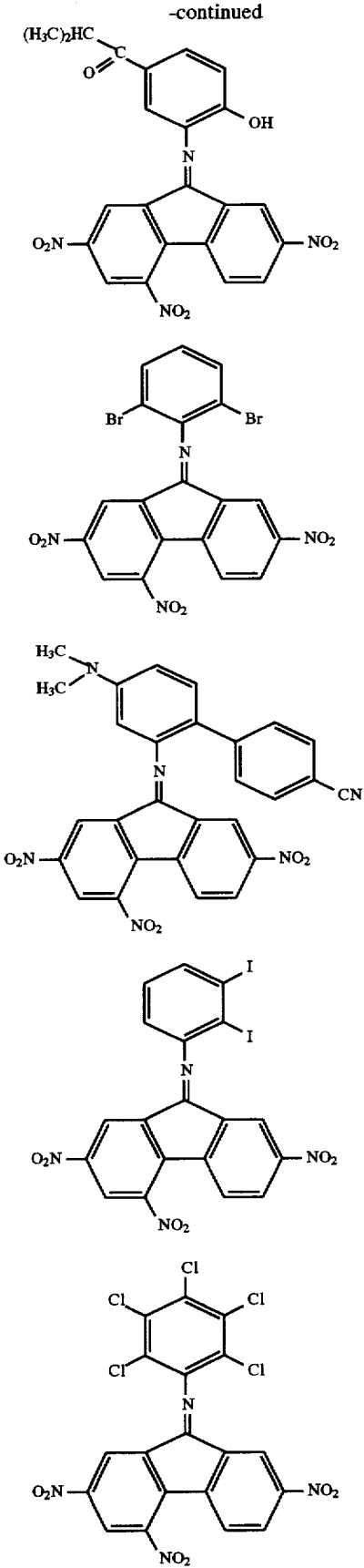
(4-9)
(4-10)
(4-11)
(4-12)
(4-13)
-continued
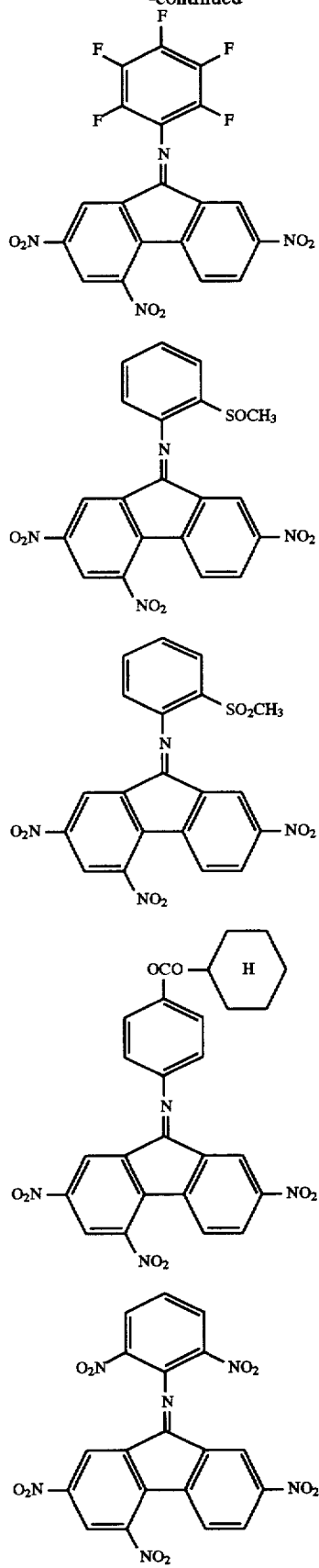
(4-14)
(4-15)
(4-16)
(4-17)
(4-18)

-continued
(4-19)
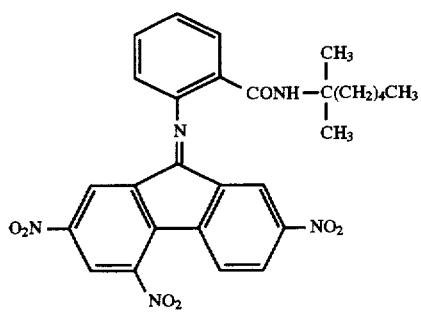
(4-20)
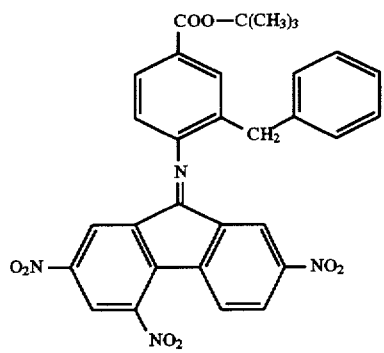
(4-21)
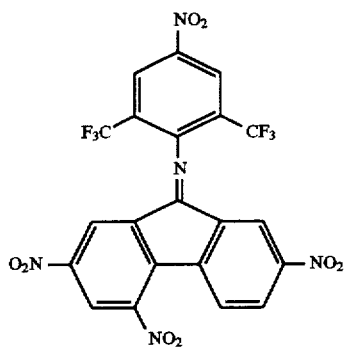
(4-22)
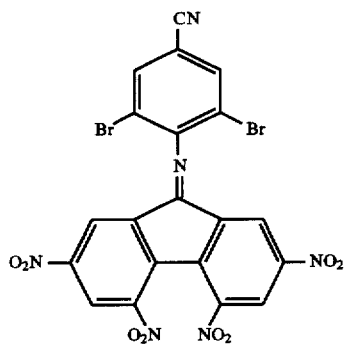
-continued
(4-23)
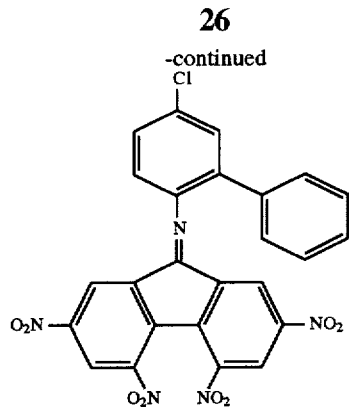
(4-24)
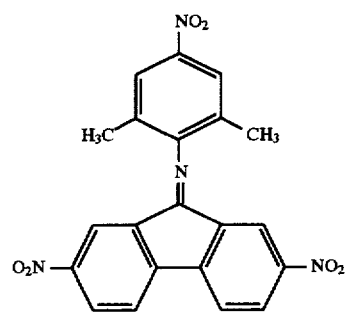
(4-25)
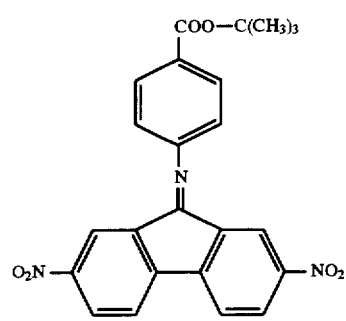
(4-26)
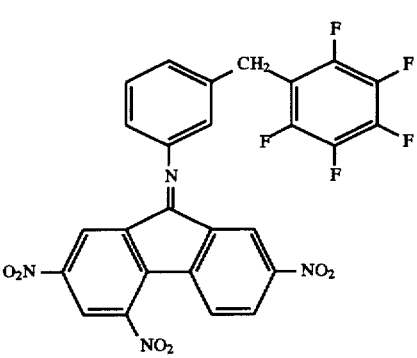
(4-27)
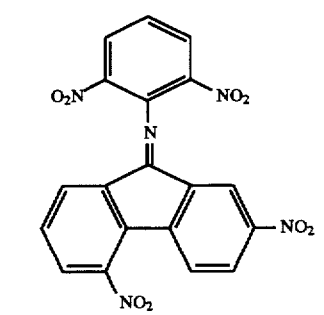

-continued

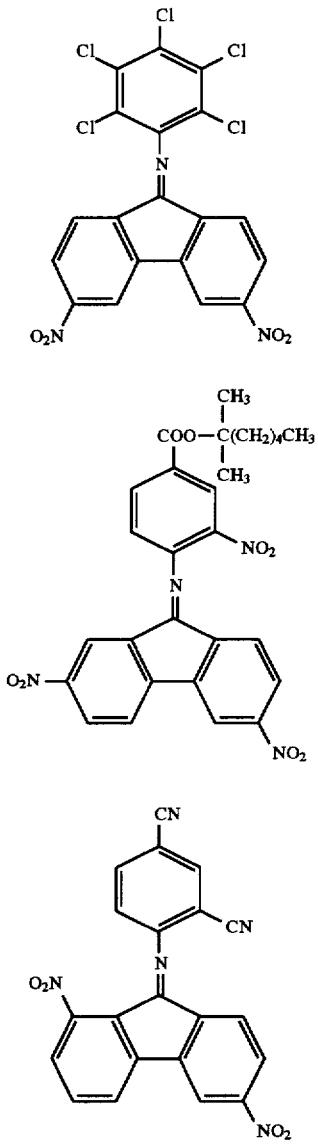

(4-28)

(4-29)

(4-30)

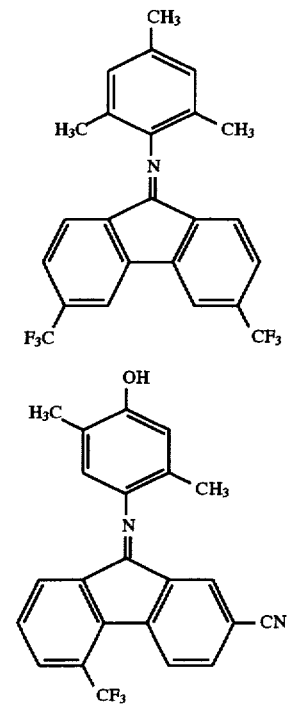

(7-4)

(7-5)

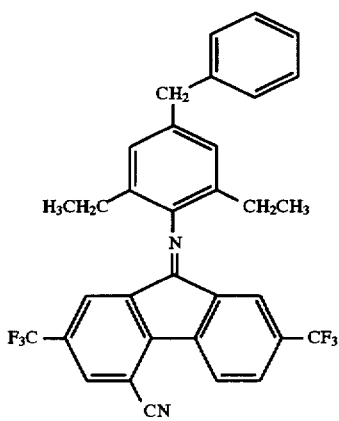

(7-6)

Comparative Examples 34 to 39

According to the same manner as that described in Examples 1 to 6 except for using 30 parts by weight of any one of the compounds represented by the above formulas (7-1) to (7-3) and compounds represented by the following formulas (7-4) to (7-6), which belong to the fluorenonimine derivative in the Publication No. 6-266128, as an electron transferring material, each electrophotosensitive material having a single-layer type photosensitive layer for digital light source was produced.

Comparative Examples 40 and 41

According to the same manner as that described in Examples 1 to 6 except for using 30 parts by weight of any one of the compounds represented by the above formulas (8-1) and (8-2) as an electron transferring material, each electrophotosensitive material having a single-layer type photosensitive layer for digital light source was produced.

Comparative Examples 42 to 45

According to the same manner as that described in Examples 1 to 6 except for using 30 parts by weight of any one of the compounds represented by the above formulas (9-1) and (9-2) and compounds represented by the following formulas (9-3) and (9-4), which belong to the fluorenonimine derivative disclosed in the Publication No. 6-266128, as an electron transferring material, each electrophotosensitive material having a single-layer type photosensitive layer for digital light source was produced.

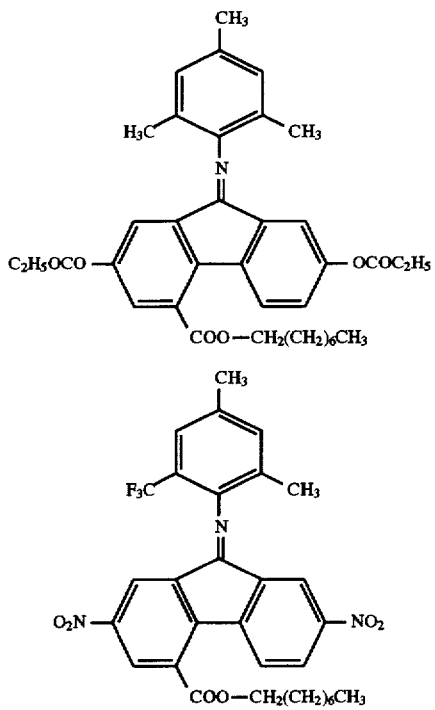
(9-3)

(9-4)

Comparative Example 46

According to the same manner as that described in Examples 1 to 6 except for using 30 parts by weight of the compound represented by the above formula (10-1) as an electron transferring material, an electrophotosensitive material having a single-layer type photosensitive layer for digital light source was produced.

Comparative Examples 47 to 54

According to the same manner as that described in Examples 1 to 6 except for using 30 parts by weight of any one of the compounds represented by the above formulas (11-1) to (11-3) and compounds represented by the following formulas (11-4) to (11-8), which belong to the fluorenonimine derivative in the Publication No. 6-266128, as an electron transferring material, each electrophotosensitive material having a single-layer type photosensitive layer for digital light source was produced.

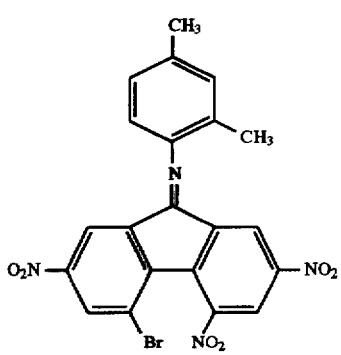
(11-4)

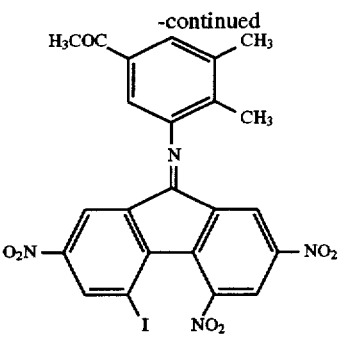
(11-5)

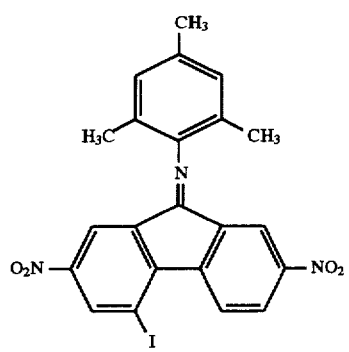
(11-6)

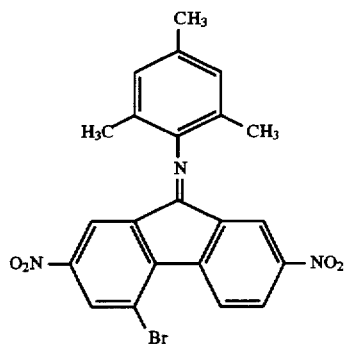
(11-7)

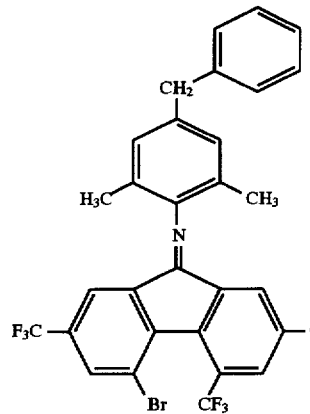
(11-8)

Comparative Examples 55 to 61

According to the same manner as that described in Examples 1 to 6 except for using 30 parts by weight of any one of the compounds represented by the above formulas (12-1) to (12-3) and compounds represented by the following formulas (12-4) to (12-7), which belong to the fluorenonimine derivative in the Publication No. 6-266128, as an electron transferring material, each electrophotosensitive material having a single-layer type photosensitive layer for digital light source was produced.

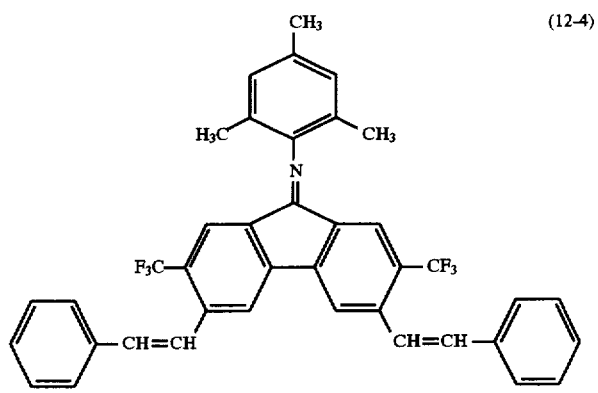

Comparative Examples 62 and 63

According to the same manner as that described in Examples 1 to 6 except for using 30 parts by weight of 3,5-dimethyl-3',5'-di-t-butyl-4,4'-diphenoquinone (DPQ) represented by the following formula (13):

as an electron transferring material, each electrophotosensitive material having a single-layer type photosensitive layer for digital light source was produced.

Comparative Example 64

According to the same manner as that described in Examples 1 to 6 except for using no electron transferring material, an electrophotosensitive material having a single-layer type photosensitive layer for digital light source was produced.

The electrophotosensitive materials of the respective Examples and Comparative Examples were subjected to the following photosensitivity test I, and their sensitivity characteristics were evaluated.

Photosensitivity test I

By using a drum sensitivity tester manufactured by GEN-TEC Co., a voltage was applied on the surface of the photosensitive materials of the respective Examples and Comparative Examples to charge its surface at +700 V. Then, monochromatic light having the wavelength of 780 nm (half-width: 20 nm) and the light intensity of 16 $\mu W/cm^2$, which was made by passing a white light of a halogen lamp being exposure light source through a band-pass filter, was irradiated on each surface of the photosensitive material for 80 msec. (irradiation time) to measure a surface potential after the elapse of 330 msec. since the beginning of exposure as a potential after exposure $V_L$ (V). The smaller the potential after exposure $V_L$ (V) is, the higher the sensitivity of the electrophotosensitive material is. The results are shown in Tables 2 to 8.

TABLE 2

|  | Electric Charge Generating Material | Electron Transferring Material | $V_L$ (V) |
| --- | --- | --- | --- |
| Example 1 | Xφ | I-1 | 132 |
| Example 2 | Xφ | II-1 | 137 |
| Example 3 | Xφ | II-2 | 138 |
| Example 4 | Tiφ | I-1 | 145 |
| Example 5 | Tiφ | II-1 | 151 |
| Example 6 | Tiφ | II-2 | 152 |
| Comp. Ex. 1 | Xφ | 3-1 | 170 |
| Comp. Ex. 2 | Xφ | 3-2 | 168 |
| Comp. Ex. 3 | Xφ | 3-3 | 164 |

TABLE 3

|         | Electric Charge Generating Material | Electron Transferring Material | $V_L$ (V) |
|---|---|---|---|
| Comp. Ex. 4  | X$\phi$ | 4-1  | 175 |
| Comp. Ex. 5  | X$\phi$ | 4-2  | 174 |
| Comp. Ex. 6  | X$\phi$ | 4-3  | 162 |
| Comp. Ex. 7  | X$\phi$ | 4-4  | 152 |
| Comp. Ex. 8  | X$\phi$ | 4-5  | 171 |
| Comp. Ex. 9  | X$\phi$ | 4-6  | 168 |
| Comp. Ex. 10 | X$\phi$ | 4-7  | 160 |
| Comp. Ex. 11 | X$\phi$ | 4-8  | 159 |
| Comp. Ex. 12 | X$\phi$ | 4-9  | 172 |
| Comp. Ex. 13 | X$\phi$ | 4-10 | 178 |

TABLE 4

|         | Electric Charge Generating Material | Electron Transferring Material | $V_L$ (V) |
|---|---|---|---|
| Comp. Ex. 14 | X$\phi$ | 4-11 | 178 |
| Comp. Ex. 15 | X$\phi$ | 4-12 | 180 |
| Comp. Ex. 16 | X$\phi$ | 4-13 | 183 |
| Comp. Ex. 17 | X$\phi$ | 4-14 | 178 |
| Comp. Ex. 18 | X$\phi$ | 4-15 | 180 |
| Comp. Ex. 19 | X$\phi$ | 4-16 | 184 |
| Comp. Ex. 20 | X$\phi$ | 4-17 | 189 |
| Comp. Ex. 21 | X$\phi$ | 4-18 | 193 |
| Comp. Ex. 22 | X$\phi$ | 4-19 | 177 |
| Comp. Ex. 23 | X$\phi$ | 4-20 | 172 |

TABLE 5

|         | Electric Charge Generating Material | Electron Transferring Material | $V_L$ (V) |
|---|---|---|---|
| Comp. Ex. 24 | X$\phi$ | 4-21 | 178 |
| Comp. Ex. 25 | X$\phi$ | 4-22 | 204 |
| Comp. Ex. 26 | X$\phi$ | 4-23 | 212 |
| Comp. Ex. 27 | X$\phi$ | 4-24 | 195 |
| Comp. Ex. 28 | X$\phi$ | 4-25 | 211 |
| Comp. Ex. 29 | X$\phi$ | 4-26 | 171 |
| Comp. Ex. 30 | X$\phi$ | 4-27 | 189 |
| Comp. Ex. 31 | X$\phi$ | 4-28 | 201 |
| Comp. Ex. 32 | X$\phi$ | 4-29 | 198 |
| Comp. Ex. 33 | X$\phi$ | 4-30 | 194 |

TABLE 6

|         | Electric Charge Generating Material | Electron Transferring Material | $V_L$ (V) |
|---|---|---|---|
| Comp. Ex. 34 | X$\phi$ | 7-1 | 241 |
| Comp. Ex. 35 | X$\phi$ | 7-2 | 251 |
| Comp. Ex. 36 | X$\phi$ | 7-3 | 259 |
| Comp. Ex. 37 | X$\phi$ | 7-4 | 273 |
| Comp. Ex. 38 | X$\phi$ | 7-5 | 263 |

TABLE 6-continued

|         | Electric Charge Generating Material | Electron Transferring Material | $V_L$ (V) |
|---|---|---|---|
| Comp. Ex. 39 | X$\phi$ | 7-6 | 244 |
| Comp. Ex. 40 | X$\phi$ | 8-1 | 198 |
| Comp. Ex. 41 | X$\phi$ | 8-2 | 227 |
| Comp. Ex. 42 | X$\phi$ | 9-1 | 206 |
| Comp. Ex. 43 | X$\phi$ | 9-2 | 283 |

TABLE 7

|         | Electric Charge Generating Material | Electron Transferring Material | $V_L$ (V) |
|---|---|---|---|
| Comp. Ex. 44 | X$\phi$ | 9-3  | 271 |
| Comp. Ex. 45 | X$\phi$ | 9-4  | 212 |
| Comp. Ex. 46 | X$\phi$ | 10-1 | 267 |
| Comp. Ex. 47 | X$\phi$ | 11-1 | 194 |
| Comp. Ex. 48 | X$\phi$ | 11-2 | 184 |
| Comp. Ex. 49 | X$\phi$ | 11-3 | 207 |
| Comp. Ex. 50 | X$\phi$ | 11-4 | 181 |
| Comp. Ex. 51 | X$\phi$ | 11-5 | 178 |
| Comp. Ex. 52 | X$\phi$ | 11-6 | 199 |
| Comp. Ex. 53 | X$\phi$ | 11-7 | 204 |

TABLE 8

|         | Electric Charge Generating Material | Electron Transferring Material | $V_L$ (V) |
|---|---|---|---|
| Comp. Ex. 44 | X$\phi$  | 11-8 | 214 |
| Comp. Ex. 55 | X$\phi$  | 12-1 | 192 |
| Comp. Ex. 56 | X$\phi$  | 12-2 | 232 |
| Comp. Ex. 57 | X$\phi$  | 12-3 | 190 |
| Comp. Ex. 58 | X$\phi$  | 12-4 | 245 |
| Comp. Ex. 59 | X$\phi$  | 12-5 | 226 |
| Comp. Ex. 60 | X$\phi$  | 12-6 | 187 |
| Comp. Ex. 61 | X$\phi$  | 12-7 | 201 |
| Comp. Ex. 62 | X$\phi$  | DPQ  | 220 |
| Comp. Ex. 63 | Ti$\phi$ | DPQ  | 242 |
| Comp. Ex. 64 | X$\phi$  | —    | 478 |

<Single-layer type photosensitive material for analog light source>

Examples 7 to 9

According to the same manner as that described in Examples 1 to 6 except for using 5 parts by weight of a perylene pigment represented by the following formula (5-1):

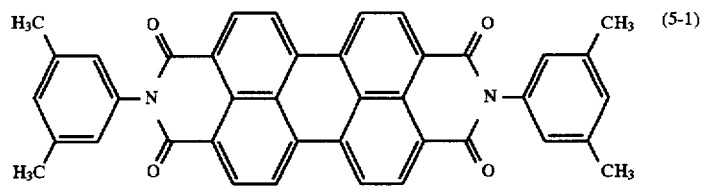

which belongs to the perylene pigment represented by the above general formula (5), as an electric charge generating material, each electrophotosensitive material having a single-layer type photosensitive layer for digital light source was produced.

Comparative Examples 65 to 67

According to the same manner as that described in Examples 7 to 9 except for using 30 parts by weight of any one of the compounds represented by the above formulas (3-1) to (3-3) as an electron transferring material, each electrophotosensitive material having a single-layer type photosensitive layer for digital light source was produced.

Comparative Examples 68 to 97

According to the same manner as that described in Examples 7 to 9 except for using 30 parts by weight of any one of the compounds represented by the above formulas (4-1) to (4-30) as an electron transferring material, each electrophotosensitive material having a single-layer type photosensitive layer for digital light source was produced.

Comparative Examples 98 to 103

According to the same manner as that described in Examples 7 to 9 except for using 30 parts by weight of any one of the compounds represented by the above formulas (7-1) to (7-6) as an electron transferring material, each electrophotosensitive material having a single-layer type photosensitive layer for digital light source was produced.

Comparative Examples 104 and 105

According to the same manner as that described in Examples 7 to 9 except for using 30 parts by weight of any one of the compounds represented by the above formulas (8-1) and (8-2) as an electron transferring material, each electrophotosensitive material having a single-layer type photosensitive layer for digital light source was produced.

Comparative Examples 106 to 109

According to the same manner as that described in Examples 7 to 9 except for using 30 parts by weight of any one of the compounds represented by the above formulas (9-1) to (9-4) as an electron transferring material, each electrophotosensitive material having a single-layer type photosensitive layer for digital light source was produced.

Comparative Example 110

According to the same manner as that described in Examples 7 to 9 except for using 30 parts by weight of the compound represented by the above formula (10-1) as an electron transferring material, an electrophotosensitive material having a single-layer type photosensitive layer for digital light source was produced.

Comparative Examples 111 to 118

According to the same manner as that described in Examples 7 to 9 except for using 30 parts by weight of any one of the compounds represented by the above formulas (11-1) to (11-8) as an electron transferring material, each electrophotosensitive material having a single-layer type photosensitive layer for digital light source was produced.

Comparative Examples 119 to 125

According to the same manner as that described in Examples 7 to 9 except for using 30 parts by weight of any one of the compounds represented by the above formulas (12-1) to (12-7) as an electron transferring material, each electrophotosensitive material having a single-layer type photosensitive layer for digital light source was produced.

Comparative Example 126

According to the same manner as that described in Examples 7 to 9 except for using 30 parts by weight of the DPQ represented by the above formula (13) as an electron transferring material, an electrophotosensitive material having a single-layer type photosensitive layer for digital light source was produced.

Comparative Example 127

According to the same manner as that described in Examples 7 to 9 except for using no electron transferring material, an electrophotosensitive material having a single-layer type photosensitive layer for digital light source was produced.

The electrophotosensitive materials of the respective Examples and Comparative Examples were subjected to the following photosensitivity test II, and their sensitivity characteristics were evaluated.

Photosensitivity test II

By using a drum sensitivity tester manufactured by GENTEC Co., a voltage was applied on the surface of the photosensitive materials of the respective Examples to charge its surface at +700 V. Then, a white light (light intensity: 147 µW/cm$^2$) of a halogen lamp being exposure light source was irradiated on the surface of the photosensitive material for 50 msec. (irradiation time) to measure the surface potential after the elapse of 330 msec. since the beginning of exposure as a potential after exposure $V_L$ (V). The smaller the potential after exposure $V_L$ (V) is, the higher the sensitivity of the electrophotosensitive material is. The results are shown in Tables 9 to 15.

TABLE 9

|  | Electric Charge Generating Material | Electron Transferring Material | $V_L$ (V) |
| --- | --- | --- | --- |
| Example 7 | 5-1 | I-1 | 224 |
| Example 8 | 5-1 | II-1 | 233 |
| Example 9 | 5-1 | II-1 | 235 |
| Comp. Ex. 65 | 5-1 | 3-1 | 244 |
| Comp. Ex. 66 | 5-1 | 3-2 | 251 |
| Comp. Ex. 67 | 5-1 | 3-3 | 248 |

TABLE 10

|  | Electric Charge Generating Material | Electron Transferring Material | $V_L$ (V) |
| --- | --- | --- | --- |
| Comp. Ex. 68 | 5-1 | 4-1 | 298 |
| Comp. Ex. 69 | 5-1 | 4-2 | 296 |
| Comp. Ex. 70 | 5-1 | 4-3 | 275 |
| Comp. Ex. 71 | 5-1 | 4-4 | 263 |
| Comp. Ex. 72 | 5-1 | 4-5 | 291 |
| Comp. Ex. 73 | 5-1 | 4-6 | 286 |
| Comp. Ex. 74 | 5-1 | 4-7 | 272 |
| Comp. Ex. 75 | 5-1 | 4-8 | 270 |
| Comp. Ex. 76 | 5-1 | 4-9 | 292 |
| Comp. Ex. 77 | 5-1 | 4-10 | 303 |

TABLE 11

| | Electric Charge Generating Material | Electron Transferring Material | $V_L$ (V) |
|---|---|---|---|
| Comp. Ex. 78 | 5-1 | 4-11 | 306 |
| Comp. Ex. 79 | 5-1 | 4-12 | 307 |
| Comp. Ex. 80 | 5-1 | 4-13 | 311 |
| Comp. Ex. 81 | 5-1 | 4-14 | 302 |
| Comp. Ex. 82 | 5-1 | 4-15 | 305 |
| Comp. Ex. 83 | 5-1 | 4-16 | 313 |
| Comp. Ex. 84 | 5-1 | 4-17 | 321 |
| Comp. Ex. 85 | 5-1 | 4-18 | 328 |
| Comp. Ex. 86 | 5-1 | 4-19 | 301 |
| Comp. Ex. 87 | 5-1 | 4-20 | 292 |

TABLE 12

| | Electric Charge Generating Material | Electron Transferring Material | $V_L$ (V) |
|---|---|---|---|
| Comp. Ex. 88 | 5-1 | 4-21 | 298 |
| Comp. Ex. 89 | 5-1 | 4-22 | 347 |
| Comp. Ex. 90 | 5-1 | 4-23 | 360 |
| Comp. Ex. 91 | 5-1 | 4-24 | 326 |
| Comp. Ex. 92 | 5-1 | 4-25 | 359 |
| Comp. Ex. 93 | 5-1 | 4-26 | 291 |
| Comp. Ex. 94 | 5-1 | 4-27 | 321 |
| Comp. Ex. 95 | 5-1 | 4-28 | 342 |
| Comp. Ex. 96 | 5-1 | 4-29 | 337 |
| Comp. Ex. 97 | 5-1 | 4-30 | 330 |

TABLE 13

| | Electric Charge Generating Material | Electron Transferring Material | $V_L$ (V) |
|---|---|---|---|
| Comp. Ex. 98 | 5-1 | 7-1 | 361 |
| Comp. Ex. 99 | 5-1 | 7-2 | 377 |
| Comp. Ex. 100 | 5-1 | 7-3 | 389 |
| Comp. Ex. 101 | 5-1 | 7-4 | 402 |
| Comp. Ex. 102 | 5-1 | 7-5 | 395 |
| Comp. Ex. 103 | 5-1 | 7-6 | 366 |
| Comp. Ex. 104 | 5-1 | 8-1 | 316 |
| Comp. Ex. 105 | 5-1 | 8-2 | 340 |
| Comp. Ex. 106 | 5-1 | 9-1 | 309 |
| Comp. Ex. 107 | 5-1 | 9-2 | 424 |

TABLE 14

| | Electric Charge Generating Material | Electron Transferring Material | $V_L$ (V) |
|---|---|---|---|
| Comp. Ex. 108 | 5-1 | 9-3 | 407 |
| Comp. Ex. 109 | 5-1 | 9-4 | 318 |
| Comp. Ex. 110 | 5-1 | 10-1 | 398 |
| Comp. Ex. 111 | 5-1 | 11-1 | 310 |
| Comp. Ex. 112 | 5-1 | 11-2 | 312 |
| Comp. Ex. 113 | 5-1 | 11-3 | 331 |
| Comp. Ex. 114 | 5-1 | 11-4 | 290 |
| Comp. Ex. 115 | 5-1 | 11-5 | 285 |
| Comp. Ex. 116 | 5-1 | 11-6 | 318 |
| Comp. Ex. 117 | 5-1 | 11-7 | 326 |

TABLE 15

| | Electric Charge Generating Material | Electron Transferring Material | $V_L$ (V) |
|---|---|---|---|
| Comp. Ex. 118 | 5-1 | 11-8 | 342 |
| Comp. Ex. 119 | 5-1 | 12-1 | 317 |
| Comp. Ex. 120 | 5-1 | 12-2 | 371 |
| Comp. Ex. 121 | 5-1 | 12-3 | 304 |
| Comp. Ex. 122 | 5-1 | 12-4 | 392 |
| Comp. Ex. 123 | 5-1 | 12-5 | 362 |
| Comp. Ex. 124 | 5-1 | 12-6 | 309 |
| Comp. Ex. 125 | 5-1 | 12-7 | 322 |
| Comp. Ex. 126 | 5-1 | DPQ | 294 |
| Comp. Ex. 127 | 5-1 | — | 521 |

Synthesis Example 4

Production of N-(3-fluoro-2-methylphenyl)-2,4,7-trinitrofluorenonimine

A 2,4,7-Trinitrofluorenonimine (3.15 g, 10 mmols) and 3-fluoro-2-methylaniline (1.88 g, 15 mmols) were dissolved in 50 ml of acetic acid, and the mixture was reacted at 110° C. for 2 hours.

After the completion of the reaction, the reaction solution was added to 300 ml of water to deposit a crystal. The crystal was filtered, washed with water, and then purified by subjecting to silica gel column chromatography (chloroform-hexane mixed system) to obtain 1.9 g of the titled compound represented by the above formula (III-1) (yield: 46%).

The melting point of this compound was 157° C.

The electron transferring capability of the above compound was evaluated by TOF method. As a result, it has been found that the compound has a high electron transferring capability because it showed the mobility of $6.81 \times 10^{-7}$ $cm^2/V.s$ at the electric field strength of $3 \times 10^5$ V/cm.

Figure 4:
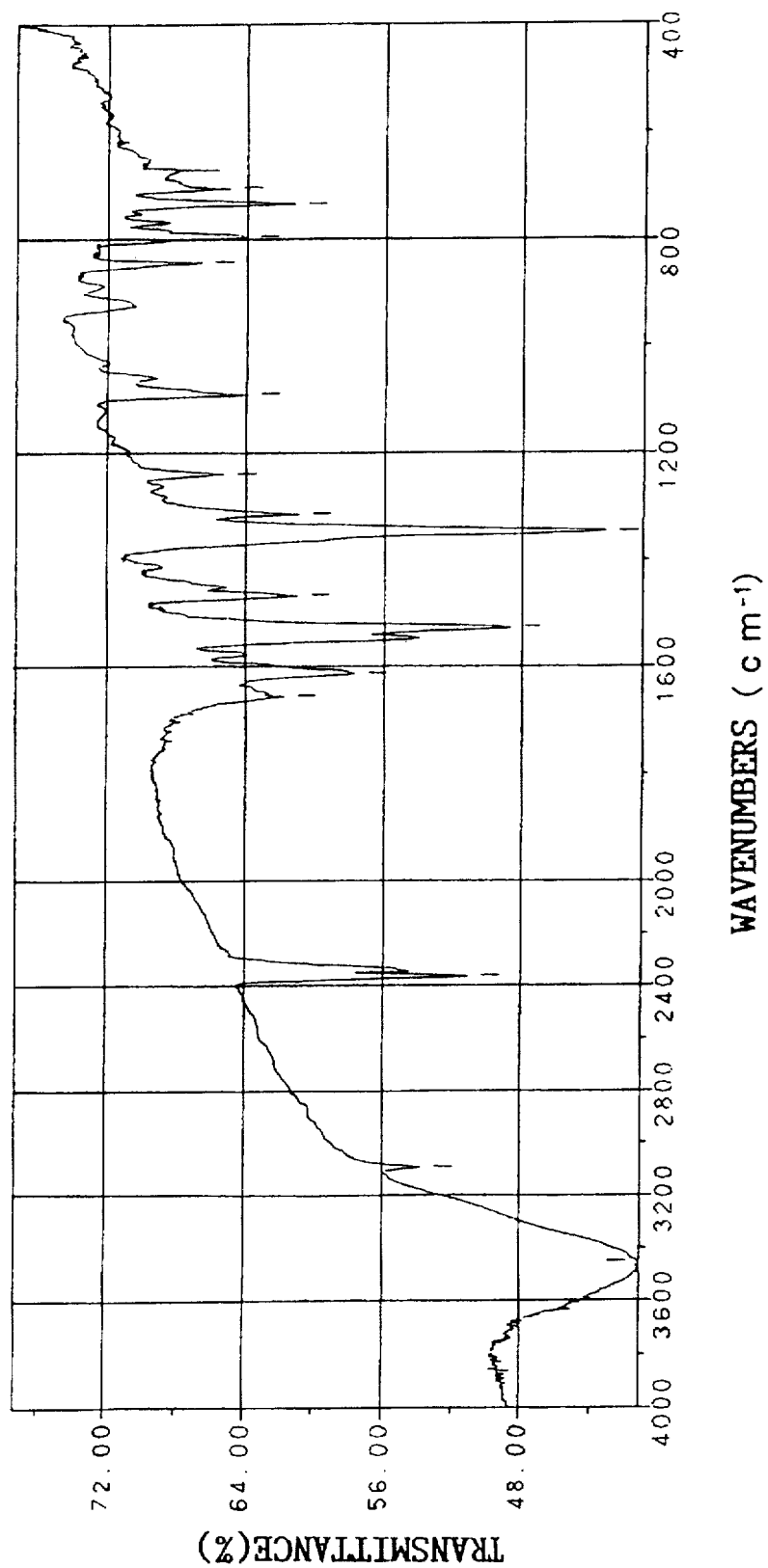

The infrared absorption spectrum of the above compound is shown in FIG. 4.

Synthesis Example 5

Production of N-(4-fluoro-2-methylphenyl)-2,4,7-trinitrofluorenonimine

According to the same manner as that described in Synthesis Example 1 except for using 4-fluoro-2-methylaniline (1.87 g, 15 mmols) in place of the 3-fluoro-2-methylaniline, 2.2 g of the titled compound represented by the above formula (III-2) was obtained (yield: 51%).

The melting point of this compound was 172° C.

The electron transferring capability of the above compound was evaluated by TOF method. As a result, it has been found that the compound has a high electron transferring capability because it showed the mobility of $4.74 \times 10^{-7}$ $cm^2/V.s$ at the electric field strength of $3 \times 10^5$ V/cm.

Figure 5:
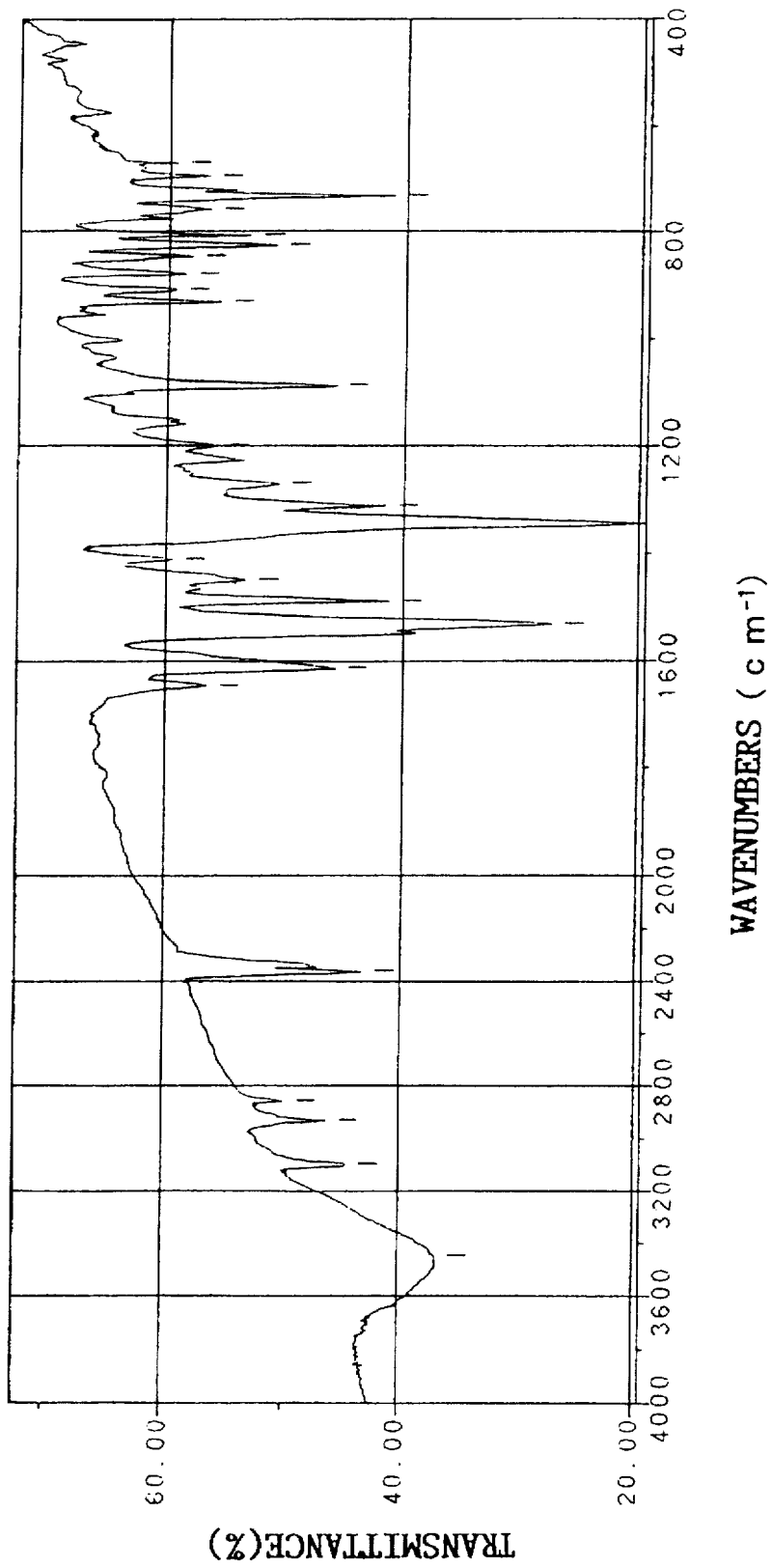

The infrared absorption spectrum of the above compound is shown in FIG. 5.

Synthesis Example 6

Synthesis of N-(5-fluoro-2-methylphenyl)-2,4,7-trinitrofluorenonimine

According to the same manner as that described in Synthesis Example 4 except for using 5-fluoro-2-methylaniline (1.88 g, 15 mmols) in place of the 3-fluoro- 2-methylaniline, 1.8 g of the titled compound represented by the above formula (III-3) was obtained (yield: 44%).

The melting point of this compound was 228° C.

The electron transferring capability of the above compound was evaluated by TOF method. As a result, it has been found that the compound has a high electron transferring capability because it showed the mobility of $5.11 \times 10^{-7}$ cm$^2$/V.s at the electric field strength of $3 \times 10^5$ V/cm.

Figure 6:
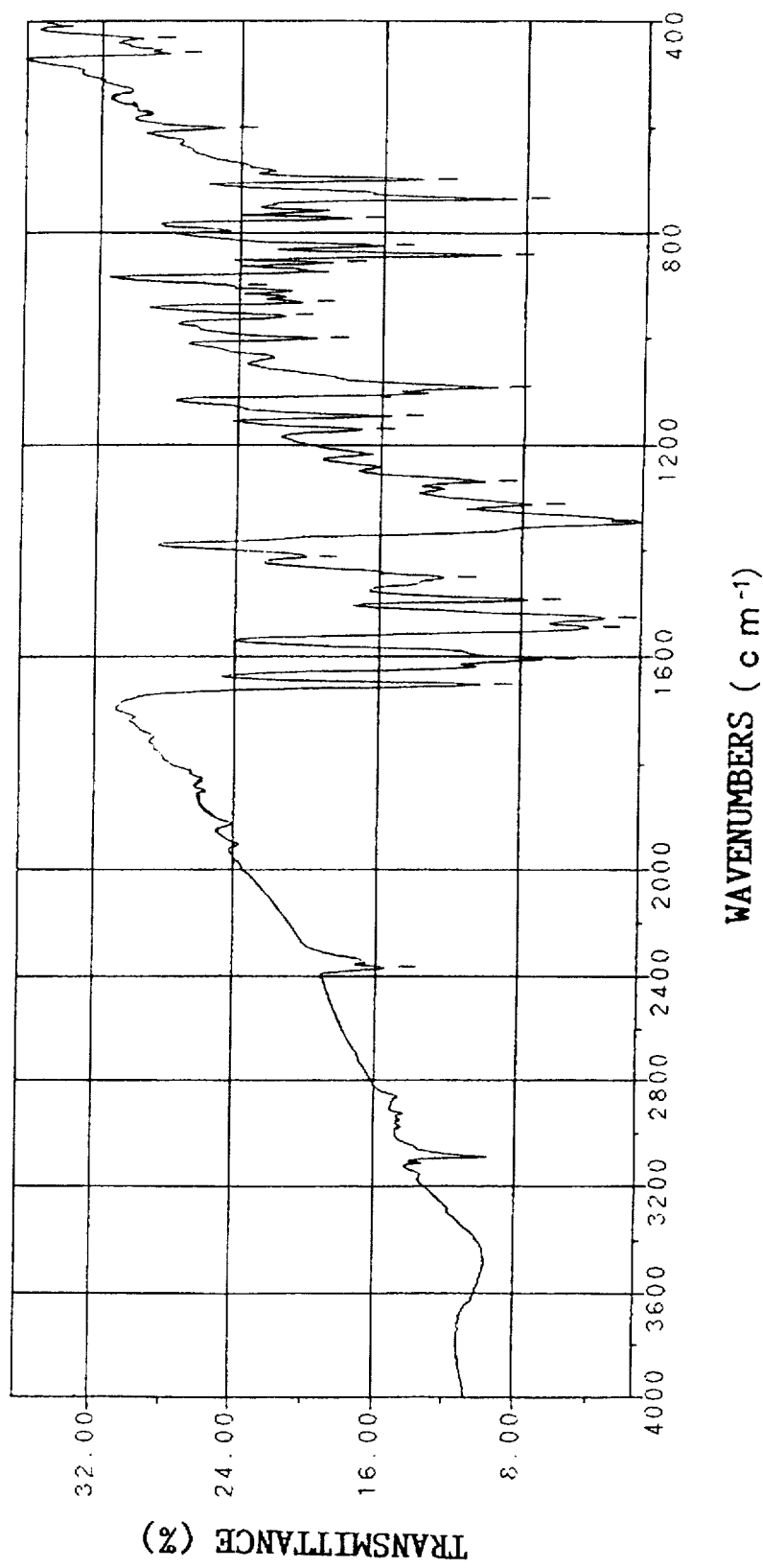

The infrared absorption spectrum of the above compound is shown in FIG. 6.

<Single-layer type photosensitive material for digital light source>

Examples 10 to 15

5 Parts by weight of X-type metal-free phthalocyanine (Xφ, Ip=5.38 eV) or oxotitanyl phthalocyanine (Tiφ, Ip=5.32 eV), 30 parts by weight of the trinitrofluorenonimine derivative represented by the above formula (II-1), (II-2) or (II-3) in Synthesis Examples 4 to 6, 50 parts by weight of N,N,N',N'-tetrakis(p-methylphenyl)-3,3'-dimethylbenzidine (Ip=5.56 eV) represented by the above formula (6), 100 parts by weight of polycarbonate and 800 parts by weight of tetrahydrofuran were mixed and dispersed using a ball mill for 50 hours to prepare a coating solution for single-layer type photosensitive layer. Then, this solution was applied on the surface of an aluminum tube being conductive substrate by dip coating, followed by hot-air drying at 100° C. for 60 minutes to obtain each electrophotosensitive material having a single-layer type photosensitive layer for digital light source, whose mean thickness is 17 μm.

The photosensitive materials of the respective Examples were subjected to the above photosensitivity test I, and their sensitivity characteristics were evaluated. The results are shown in Table 16, in which those of Comparative Examples 1 to 3 are also shown.

TABLE 16

| | Electric Charge Generating Material | Electron Transferring Material | $V_L$ (V) |
|---|---|---|---|
| Example 10 | Xφ | III-1 | 132 |
| Example 11 | Xφ | III-2 | 127 |
| Example 12 | Xφ | III-3 | 129 |
| Example 13 | Tiφ | III-1 | 145 |
| Example 14 | Tiφ | III-2 | 140 |
| Example 15 | Tiφ | III-3 | 142 |
| Comp. Ex. 1 | Xφ | 3-1 | 170 |
| Comp. Ex. 2 | Xφ | 3-2 | 168 |
| Comp. Ex. 3 | Xφ | 3-3 | 164 |

Wear Resistance Test

The wear resistance of the photosensitive materials of Examples 10 to 12 and the respective Comparative Examples shown in Table 17 was evaluated by the following test method.

<Test method>

A test photosensitive material was fit with an imaging unit of a facsimile apparatus for plain paper (Model LDC-650, manufactured by Mita Industrial Co., Ltd.), and after the rotation of 150,000 times without passing a paper through it, the amount of wear (μm) of the photosensitive layer was determined. The results are shown in Table 17.

TABLE 17

| Example No. | Amount of Wear(m) |
|---|---|
| Example 10 | 3.1 |
| Example 11 | 2.9 |
| Example 12 | 3.3 |
| Comp. Ex. 1 | 4.9 |
| Comp. Ex. 2 | 5.1 |
| Comp. Ex. 3 | 5.0 |
| Comp. Ex. 6 | 6.1 |
| Comp. Ex. 7 | 5.3 |
| Comp. Ex. 8 | 5.2 |
| Comp. Ex. 11 | 4.9 |
| Comp. Ex. 16 | 4.0 |
| Comp. Ex. 17 | 3.3 |
| Comp. Ex. 23 | 5.6 |
| Comp. Ex. 24 | 4.1 |
| Comp. Ex. 28 | 5.8 |
| Comp. Ex. 29 | 3.2 |
| Comp. Ex. 32 | 5.7 |

<Single-layer photosensitive material for analog light source>

Examples 16 to 18

According to the same manner as that described in Examples 10 to 15 except for using the perylene pigment represented by the above formula (5-1) as an electric charge generating material, each electrophotosensitive material having a single-layer type photosensitive layer for analog light source was produced.

The electrophotosensitive materials of the respective Examples and Comparative Examples were subjected to the above photosensitivity test II, and each sensitivity was evaluated. The results are shown in Table 18, in which those of Comparative Examples 65 to 67 are also shown.

TABLE 18

| | Electric Charge Generating Material | Electron Transferring Material | $V_L$ (V) |
|---|---|---|---|
| Example 16 | 5-1 | III-1 | 224 |
| Example 17 | 5-1 | III-2 | 216 |
| Example 18 | 5-1 | III-3 | 219 |
| Example 65 | 5-1 | 3-1 | 244 |
| Example 66 | 5-1 | 3-2 | 251 |
| Example 67 | 5-1 | 3-3 | 248 |

Synthesis Example 7

Production of N-(2-methyl-6-ethylphenyl)-2,4,7-trinitrofluorenonimine

A 2,4,7-Trinitrofluorenonimine (3.15 g, 10 mmols) and 2-methyl-6-ethylaniline (2.03 g, 15 mmols) were dissolved in 50 ml of acetic acid, and the mixture was reacted at 110° C. for 2 hours.

After the completion of the reaction, the reaction solution was added to 300 ml of water to deposit a crystal. The crystal was filtered, washed with water, and then purified by subjecting to silica gel column chromatography (chloroform-hexane mixed system) to obtain 2.6 g of the titled compound represented by the above formula (IV-1) (yield: 60%).

The melting point of this compound was 201° C.

The electron transferring capability of the above compound was evaluated by TOF method. As a result, it has been found that the compound has a high electron transferring capability because it showed the mobility of $6.42 \times 10^{-7}$ cm$^2$/V.s at the electric field strength of $3 \times 10^5$ V/cm.

Figure 7:
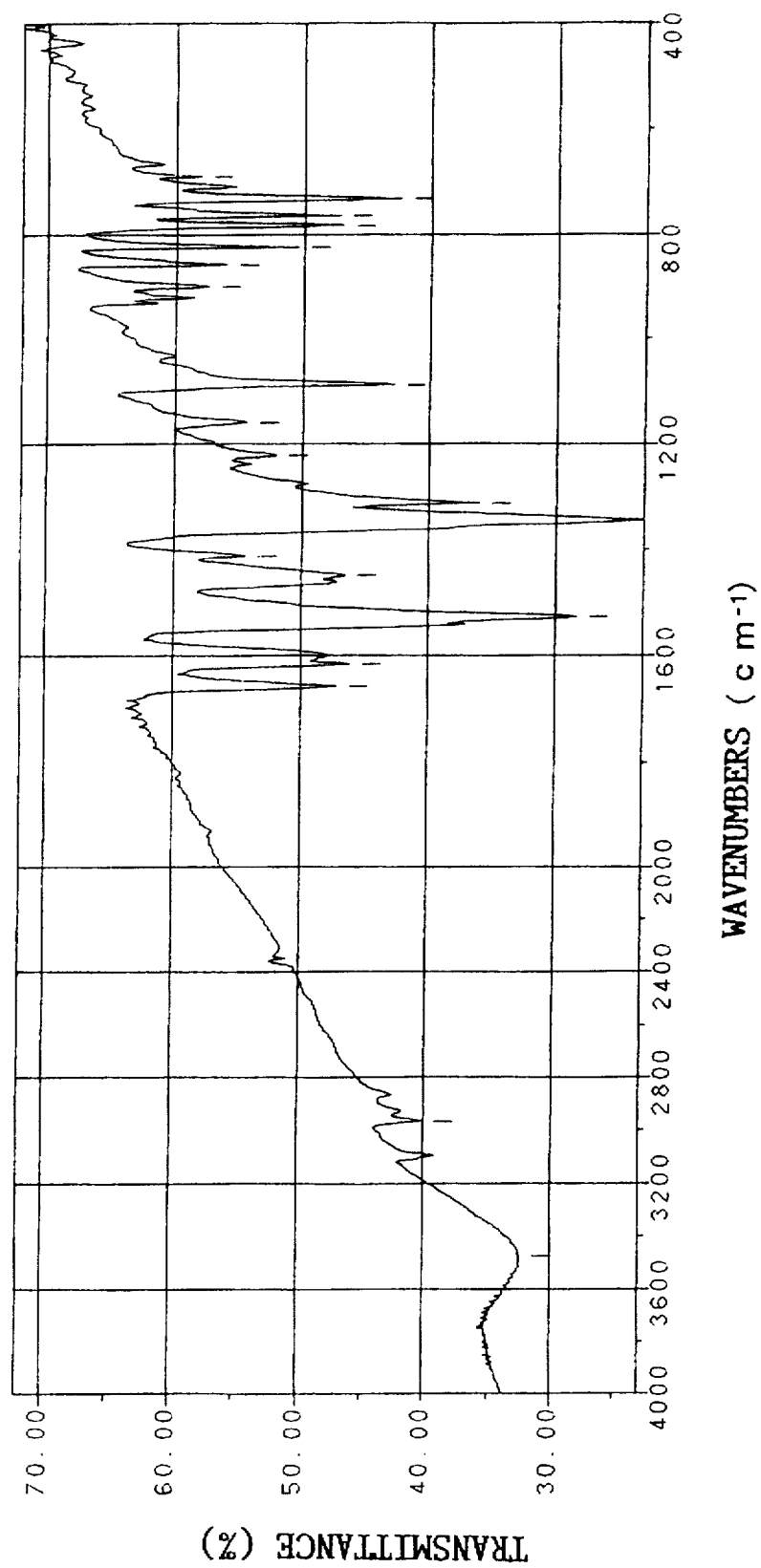

The infrared absorption spectrum of the above compound is shown in FIG. 7.

Synthesis Example 8

Production of N-(2-methyl-6-isopropylphenyl)-2,4,7-trinitrofluorenonimine

According to the same manner as that described in Synthesis Example 7 except for using 2-methyl-6-isopropylaniline (2.25 g, 15 mmols) in place of the 2-methyl-6-ethylaniline, 2.6 g of the titled compound represented by the above formula (IV-2) was obtained (yield: 58%).

The melting point of this compound was 199° C.

The electron transferring capability of the above compound was evaluated by TOF method. As a result, it has been found that the compound has a high electron transferring capability because it showed the mobility of $5.91 \times 10^{-7}$ cm$^2$/V.s at the electric field strength of $3 \times 10^5$ V/cm.

Figure 8:
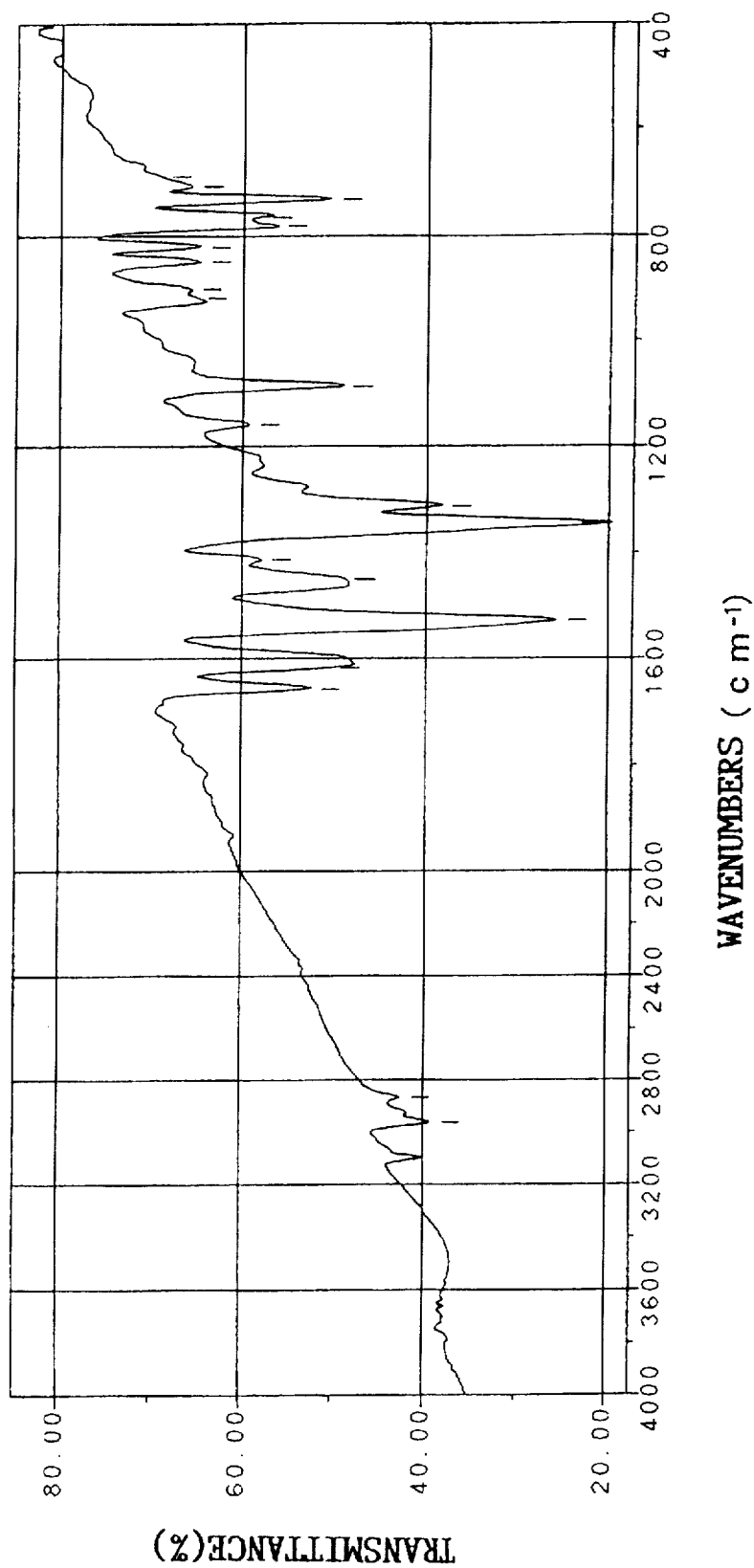

The infrared absorption spectrum of the above compound is shown in FIG. 8.

Solubility and Compatibility tests

The solubility in tetrahydrofuran and the compatibility with polycarbonate of the compounds in Synthesis Examples 7 and 8 were evaluated according to the same test methods as described above. The results are shown in Table 19.

The compounds shown in Table 19 were used as a test comparative compound. The compound test (14-1) is represented by the following formula (14-1):

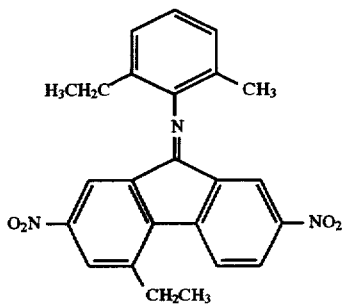

which belongs to the fluorenonimine derivative in the Publication No. 6-266128.

TABLE 19

| Test Compound | Solubility | Compatibility |
|---|---|---|
| IV-1 | ○ | ○ |
| IV-1 | ○ | ○ |
| 3-1 | ○ | Δ |
| 3-2 | ○ | Δ |
| 3-3 | ○ | Δ |
| 4-2 | × | × |
| 4-4 | Δ | × |
| 4-5 | Δ | × |
| 4-24 | Δ | × |
| 14-1 | Δ | × |

<Single-layer type photosensitive material for digital light source>

Examples 19 to 22

5 Parts by weight of X-type metal-free phthalocyanine (Xφ, Ip=5.38 eV) or oxotitanyl phthalocyanine (Tiφ, Ip=5.32 eV) as an electric charge generating material, 30 parts by weight of the trinitrofluorenonimine derivative represented by the above formula (IV-1) or (IV-2) in Synthesis Examples 7 and 8 as an electron transferring material, 50 parts by weight of N,N,N',N'-tetrakis(p-methylphenyl)-3,3'-dimethylbenzidine (Ip=5.56 eV) represented by the above formula (6) as a hole transferring material, 100 parts by weight of polycarbonate and 800 parts by weight of tetrahydrofuran were mixed and dispersed using a ball mill for 50 hours to prepare a coating solution for single-layer type photosensitive layer. Then, this solution was applied on the surface of an aluminum tube being conductive substrate by dip coating, followed by hot-air drying at 100° C. for 60 minutes to obtain each electrophotosensitive material having a single-layer type photosensitive layer for digital light source, whose mean thickness is 17 μm.

Comparative Example 128

According to the same manner as that described in Examples 19 to 22 except for using 30 parts by weight of the compound represented by the above formula (14-1) as an electron transferring material, an electrophotosensitive material having a single-layer type photosensitive layer for digital light source was produced.

The electrophotosensitive materials of the above respective Examples and Comparative Examples were subjected to the above photosensitivity test I, and each sensitivity was evaluated. The results are shown in Table 20, in which those of Comparative Examples 1 to 3 are also shown.

TABLE 20

| | Electric Charge Generating Material | Electron Transferring Material | $V_L$ (V) |
|---|---|---|---|
| Example 19 | Xφ | IV-1 | 133 |
| Example 20 | Xφ | IV-2 | 130 |
| Example 21 | Tiφ | IV-1 | 146 |
| Example 22 | Tiφ | IV-2 | 143 |
| Comp. Ex. 1 | Xφ | 3-1 | 170 |
| Comp. Ex. 2 | Xφ | 3-2 | 168 |
| Comp. Ex. 3 | Xφ | 3-3 | 164 |
| Comp. Ex. 128 | Xφ | 14-1 | 189 |

<Single-layer type photosensitive material for analog light source>

Examples 23 and 24

According to the same manner as that described in Examples 19 to 22 except for using 5 parts by weight of the perylene pigment represented by the above formula (5-1) as an electric charge generating material, each electrophotosensitive material having a single-layer type photosensitive layer for analog light source was produced.

Comparative Example 129

According to the same manner as that described in Examples 23 and 24 except for using 30 parts by weight of the compound represented by the above formula (14-1) as an electron transferring material, an electrophotosensitive material having a single-layer type photosensitive layer for digital light source was produced.

The electrophotosensitive materials of the above respective Examples and Comparative Examples were subjected to the above photosensitivity test II, and each sensitivity was evaluated. The results are shown in Table 21, in which those of Comparative Examples 65 to 67 are also shown.

TABLE 21

| | Electric Charge Generating Material | Electron Transferring Material | $V_L$ (V) |
|---|---|---|---|
| Example 23 | Xφ | IV-1 | 226 |
| Example 24 | 5-1 | IV-2 | 221 |
| Comp. Ex. 65 | 5-1 | 3-1 | 244 |
| Comp. Ex. 66 | 5-1 | 3-2 | 251 |
| Comp. Ex. 67 | 5-1 | 3-3 | 248 |
| Comp. Ex. 129 | 5-1 | 14-1 | 311 |

What is claimed is:

1. An electrophotosensitive material comprising a conductive substrate and a photosensitive layer provided on the conductive substrate, the photosensitive layer containing the trinitrofluorenonimine derivative of the general formula (I):

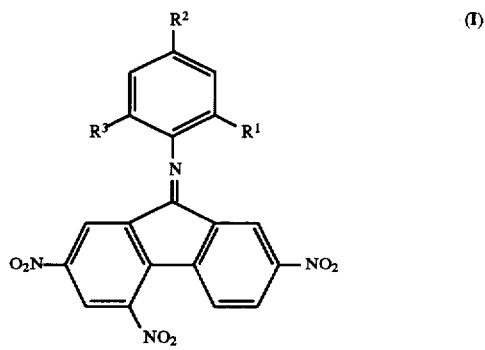

wherein $R^1$, $R^2$ and $R^3$ are the same or different and indicate an alkyl group which may have a substituent, in a binding resin.

2. An electrophotosensitive material comprising a conductive substrate and a photosensitive layer provided on the conductive substrate, the photosensitive layer containing the trinitrofluorenonimine derivative of the general formula (II)

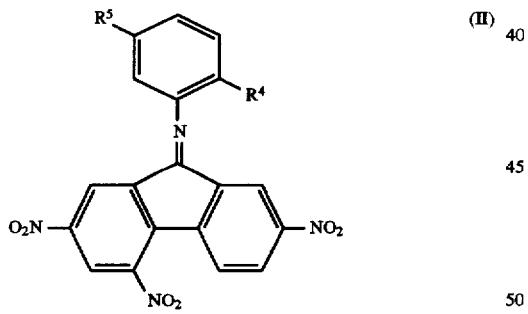

wherein $R^4$ and $R^5$ are the same or different and indicate an alkyl group which may have a substituent, in a binding resin.

3. An electrophotosensitive material comprising a conductive substrate and a photosensitive layer provided on the conductive substrate, the photosensitive layer containing the trinitrofluorenonimine derivative of the general formula (III)

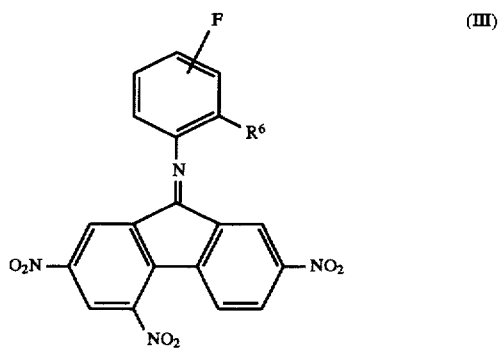

wherein $R^6$ is an alkyl group which may have a substituent, in a binding resin.

4. An electrophotosensitive material comprising a conductive substrate and a photosensitive layer provided on the conductive substrate, the photosensitive layer containing the trinitrofluorenonimine derivative of the general formula (IV)

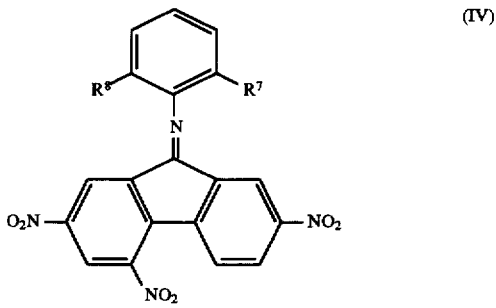

wherein $R^7$ and $R^8$ are different and indicate an alkyl croup which may have a substituent, in a binding resin.

* * * * *